United States Patent
Jo et al.

(10) Patent No.: US 11,976,279 B2
(45) Date of Patent: May 7, 2024

(54) METHODS AND COMPOSITIONS FOR MANAGING VASCULAR CONDITIONS USING MIR-483 MIMICS AND HIF1ALPHA PATHWAY INHIBITORS

(71) Applicant: Emory University, Atlanta, GA (US)

(72) Inventors: Hanjoong Jo, Atlanta, GA (US); Joan Fernandez Esmerats, Atlanta, GA (US); Nicolas Villa-Roel, Brookhaven, GA (US)

(73) Assignee: Emory University, Atlanta, GA (US)

( * ) Notice: Subject to any disclaimer, the term of this patent is extended or adjusted under 35 U.S.C. 154(b) by 128 days.

(21) Appl. No.: 17/544,801

(22) Filed: Dec. 7, 2021

(65) Prior Publication Data

US 2022/0090079 A1    Mar. 24, 2022

Related U.S. Application Data

(62) Division of application No. 16/156,917, filed on Oct. 10, 2018, now Pat. No. 11,225,660.

(60) Provisional application No. 62/571,446, filed on Oct. 12, 2017.

(51) Int. Cl.
| | |
|---|---|
| *C07H 21/04* | (2006.01) |
| *A61K 31/198* | (2006.01) |
| *A61K 31/713* | (2006.01) |
| *A61K 45/06* | (2006.01) |
| *C12N 15/113* | (2010.01) |

(52) U.S. Cl.
CPC .......... *C12N 15/113* (2013.01); *A61K 31/198* (2013.01); *A61K 31/713* (2013.01); *A61K 45/06* (2013.01); *C12N 2310/113* (2013.01); *C12N 2310/14* (2013.01); *C12N 2310/141* (2013.01); *C12N 2310/3231* (2013.01); *C12N 2320/31* (2013.01)

(58) Field of Classification Search
None
See application file for complete search history.

(56) References Cited

U.S. PATENT DOCUMENTS

| | | |
|---|---|---|
| 7,427,672 B2 | 9/2008 | Imanishi |
| 11,225,660 B2 | 1/2022 | Jo |
| 2003/0176317 A1 | 9/2003 | Guenzler-Pukall |
| 2005/0049309 A1 | 3/2005 | Kirkpatrick |
| 2012/0165392 A1 | 6/2012 | Olson |
| 2015/0141495 A1 | 5/2015 | Port |
| 2016/0002628 A1 | 1/2016 | Jo |

FOREIGN PATENT DOCUMENTS

WO    2013127782    9/2013

OTHER PUBLICATIONS

Koransky, Mark L., Robert C. Robbins, and Helen M. Blau. "VEGF gene delivery for treatment of ischemic cardiovascular disease." Trends in cardiovascular medicine 12.3 (2002): 108-114.*
Qiao, Yu, et al. "miR-483-3p regulates hyperglycemia-induced cardiomyocyte apoptosis in transgenic mice." Biochemical and biophysical research communications 477.4 (2016): 541-547.*
Ajami et al. Systems biology analysis of longitudinal functional response of endothelial cells to shear stress, Proc Natl Acad Sci U S A, 2017, 114(41):10990-10995.
Akin et al. Is there evidence for statins in the treatment of aortic valve stenosis? World J Cardiol 2017; 9(8): 667-672.
Anandhi et al. Evaluation of the anti-atherogenic potential of chrysin in Wistar rats, Mol Cell Biochem (2014) 385:103-113.
Esmerats et al. Shear-Sensitive Genes in Aortic Valve Endothelium, Antioxid. Redox Signal. 2016, 25, 401-414.
Esmerats et al. Disturbed flow increases UBE2C via loss of miR-483-3p, inducing aortic valve calcification by the HIF1α pathway in endothelial cells, Arterioscler Thromb Vasc Biol. 2019, 39(3): 467-481.
Garbacki et al., MicroRNAs Profiling in Murine Models of Acute and Chronic Asthma: A Relationship with mRNAs Targets, Targets. PLoS One, 2011, 6(1): e16509.
Gosev et al. Epigenome alterations in aortic valve stenosis and its related left ventricular hypertrophy, Clinical Epigenetics (2017) 9:106.
He et al. miR-483 Targeting of CTGF Suppresses Endothelial-to-Mesenchymal Transition: Therapeutic Implications in Kawasaki Disease, Circ Res. 2017, 120(2): 354-365.
Heath et al. Role of miRNA-483-3p in Valvular Endothelial Dysfunction, HVS Scientific Meeting 2016.
Hiatt Atherosclerotic Peripheral Vascular Disease Symposium II Nomenclature for Vascular Diseases, Circulation. 2008;118:2826-2829.
Holliday et al. Discovery of shear- and side-specific mRNAs and miRNAs in human aortic valvular endothelial cells, Am J Physiol Heart Circ Physiol. 2011, 301(3): H856-H867.
Holliday et al. The function of shear-responsive and side-dependent microRNA-486-5p in aortic valve endothelium, Abstracts / Cardiovascular Pathology 22 (2013) e29-e52.
Kim et al. MicroRNAs as critical regulators of the endothelial to mesenchymal transition in vascular biology, BMB Rep. 2018; 51(2): 65-72.

(Continued)

*Primary Examiner* — Kimberly Chong
(74) *Attorney, Agent, or Firm* — Emory Patent Group

(57) ABSTRACT

This disclosure relates to the use of miRNA-483 and its target genes, UBE2C, pVHL and HIF1alpha, in managing the treatment of cardiovascular and inflammatory diseases. In certain embodiments, this disclosure relates to pharmaceutical compositions comprising a miR-483 mimic and/or an HIF inhibitor and a pharmaceutically acceptable excipient for use in treating or preventing a vascular disease or condition. In certain embodiments, the miR-483 mimic is a double stranded nucleobase polymer or an expression vector that expresses mature human miR-483-5p and miR-483-3p sequences or operable fragments and variants.

8 Claims, 11 Drawing Sheets

Specification includes a Sequence Listing.

(56) References Cited

OTHER PUBLICATIONS

Leal et al. Rheumatic heart disease in the modern era: recent developments and current challenges, Rev Soc Bras Med Trop vol. 52:e-20180226, 2019.

Lee et al. A Novel Approach to Cancer Therapy using PX-478 as a HIF-1α Inhibitor, Arch Pharm Res vol. 34, No. 10, 1583-1585, 2011.

Lim et al. Hypoxia-inducible factor pathway and diseases of the vascular wall, J Vasc Surg, 2013;58:219-30.

Marsch et al. Hypoxia in atherosclerosis and inflammation, Curr Opin Lipidol 2013, 24:393-400.

Perrotta et al. HIF-1α and VEGF: Immunohistochemical Profile and Possible Function in Human Aortic Valve Stenosis, Ultrastructural Pathology, 2015, 39:3, 198-206.

Perrotta et al. Ultrastructural, Elemental and Mineralogical Analysis of Vascular Calcification in Atherosclerosis, Microsc. Microanal. 23, 1030-1039, 2017.

Rathan et al. Identification of side- and shear-dependent microRNAs regulating porcine aortic valve pathogenesis, Scientific Reports vol. 6, Article No. 25397 (2016).

Sathyamurthy et al. Calcific aortic valve disease: Is it another face of atherosclerosis? Indian Heart Journal, 67 (2015) 503-506.

Simmons et al. New Insights into Mechanical Regulation of Valve Disease and Regeneration, Cardiovascular Engineering and Technology, 2018, 9(2) 121-125.

Tang et al. Small molecules targeting HIF-1α pathway for cancer therapy in recent years, Bioorganic & Medicinal Chemistry 28 (2020) 115-235.

Vaughan et al. The Evolving Role of Statins in the Management of Atherosclerosis, J Am Coll Cardiol 2000, 35:1-10.

Wang et al. MicroRNA Expression Signature in Human Calcific Aortic Valve Disease, BioMed Research International vol. 2017, Article ID 4820275, 7.

Yu et al. Development of Inhibitors Targeting Hypoxia-Inducible Factor 1 and 2 for Cancer Therapy, Yonsei Med J 2017, 58(3):489-496.

\* cited by examiner

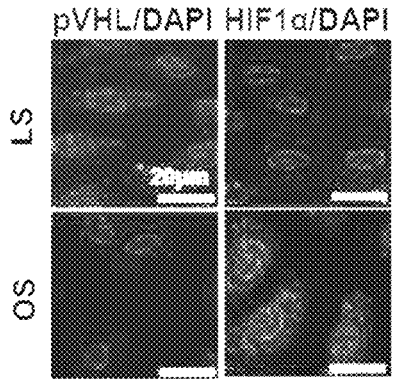
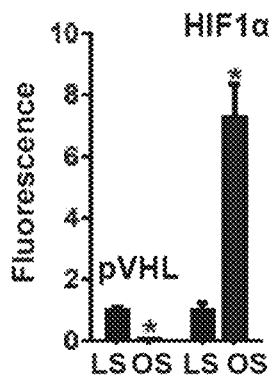
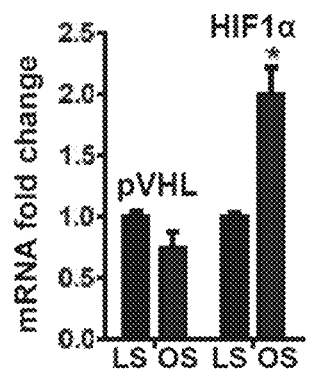
FIG. 3B
FIG. 3C
FIG. 3D
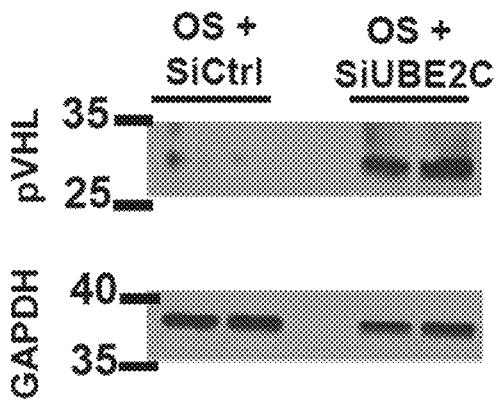
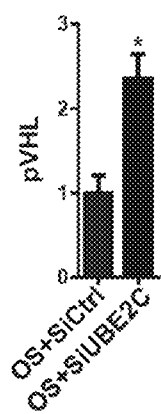
FIG. 3E
FIG. 3F
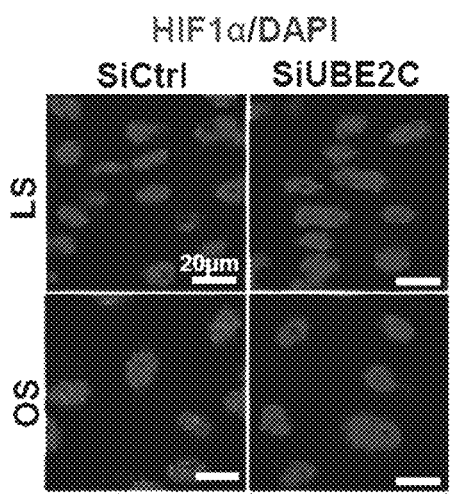
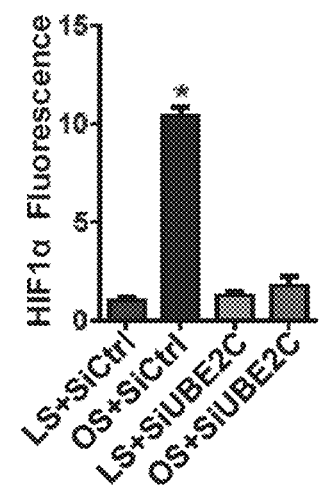
FIG. 3G
FIG. 3H

SEQUENCE LISTING

```
<160> NUMBER OF SEQ ID NOS: 11

<210> SEQ ID NO 1
<211> LENGTH: 22
<212> TYPE: DNA
<213> ORGANISM: Artificial
<220> FEATURE:
<223> OTHER INFORMATION: Synthetic construct

<400> SEQUENCE: 1
aagacgggag gaaagaaggg ag                                              22

<210> SEQ ID NO 2
<211> LENGTH: 21
<212> TYPE: DNA
<213> ORGANISM: Artificial
<220> FEATURE:
<223> OTHER INFORMATION: Synthetic construct
```

-continued

```
<400> SEQUENCE: 2
ucacuccucu ccucccgucu u                                        21

<210> SEQ ID NO 3
<211> LENGTH: 76
<212> TYPE: DNA
<213> ORGANISM: Artificial
<220> FEATURE:
<223> OTHER INFORMATION: Synthetic construct

<400> SEQUENCE: 3
gagggggaag acgggaggaa agaagggagu gguuccauca cgccuccuca cuccucuccu    60
cccgucuucu ccucuc                                              76

<210> SEQ ID NO 4
<211> LENGTH: 11
<212> TYPE: DNA
<213> ORGANISM: Artificial
<220> FEATURE:
<223> OTHER INFORMATION: Synthetic construct

<400> SEQUENCE: 4
ucacuccucu c                                                   11

<210> SEQ ID NO 5
<211> LENGTH: 10
<212> TYPE: DNA
<213> ORGANISM: Artificial
<220> FEATURE:
<223> OTHER INFORMATION: Synthetic construct

<400> SEQUENCE: 5
cucccgucuu                                                     10

<210> SEQ ID NO 6
<211> LENGTH: 11
<212> TYPE: DNA
<213> ORGANISM: Artificial
<220> FEATURE:
<223> OTHER INFORMATION: Synthetic construct

<400> SEQUENCE: 6
aagacgggag g                                                   11

<210> SEQ ID NO 7
<211> LENGTH: 11
<212> TYPE: DNA
<213> ORGANISM: Artificial
<220> FEATURE:
<223> OTHER INFORMATION: Synthetic construct

<400> SEQUENCE: 7
aaagaaggga g                                                   11

<210> SEQ ID NO 8
<211> LENGTH: 6
<212> TYPE: DNA
<213> ORGANISM: Artificial
<220> FEATURE:
<223> OTHER INFORMATION: Synthetic construct

<400> SEQUENCE: 8 aagacg                                                         6
```

```
<210> SEQ ID NO 9
<211> LENGTH: 16
<212> TYPE: DNA
<213> ORGANISM: Artificial
<220> FEATURE:
<223> OTHER INFORMATION: Synthetic construct

<400> SEQUENCE: 9
ggaggaaaga agggag                                                    16

<210> SEQ ID NO 10
<211> LENGTH: 6
<212> TYPE: DNA
<213> ORGANISM: Artificial
<220> FEATURE:
<223> OTHER INFORMATION: Synthetic construct

<400> SEQUENCE: 10 ucacuc                                                                6

<210> SEQ ID NO 11
<211> LENGTH: 15
<212> TYPE: DNA
<213> ORGANISM: Artificial
<220> FEATURE:
<223> OTHER INFORMATION: Synthetic construct

<400> SEQUENCE: 11
cucuccuccc gucuu                                                     15
```

METHODS AND COMPOSITIONS FOR MANAGING VASCULAR CONDITIONS USING MIR-483 MIMICS AND HIF1ALPHA PATHWAY INHIBITORS

CROSS-REFERENCE TO RELATED APPLICATIONS

This application is a division of U.S. application Ser. No. 16/156,917 filed Oct. 10, 2018, which claims the benefit of U.S. Provisional Application No. 62/571,446 filed Oct. 12, 2017. The entirety of each of these applications is hereby incorporated by reference for all purposes.

STATEMENT REGARDING FEDERALLY SPONSORED RESEARCH OR DEVELOPMENT

This invention was made with government support under HL119798 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 18014US_ST25.txt. The text file is 3 KB, was created on Oct. 10, 2018, and is being submitted electronically via EFS-Web.

BACKGROUND

Old age is a risk factor for developing vascular sclerosis and calcification. Calcific aortic valve disease (CAVD) is identified by calcium-rich nodules on the aortic surface or within the valve area, leading to sclerosis and ventricular outflow obstruction. Surgical valve replacement is currently the sole treatment option. Histological features of CAVD are similar to what occurs in vascular atherosclerosis. However, traditional atherosclerosis treatments, such as lipid-lowering therapy with statins, do not alone appear to be satisfactory. Therefore, there is a need to identify improved therapies.

Heath et al. report mechanosensitive microRNA-181b regulates aortic valve endothelial matrix degradation by targeting TIMP3. Cardiovasc Eng Technol. 2018, 9(2):141-150. See also U.S. Patent Application Publication No. 20160002628. Holliday et al report shear- and side-specific mRNAs and miRNAs in human aortic valvular endothelial cells. Am. J. Physiol. Heart Circ. Physiol. 301:H856-H867, 2011. Rathan et al. report side- and shear-dependent microRNAs regulating porcine aortic valve pathogenesis. Sci. Rep. 6:25397, 2016. Simmons et al. report on heart valve mechanobiology. Cardiovasc Eng Technol. 2018, 9(2):121-125.

He et al. report miR-483 targeting of CTGF has implications in Kawasaki Disease. Circ Res 120, 354-365 (2017). MicroRNA-483 was reported to target to the 3'UTR of murine UBE2C. Garback et al., MicroRNAs Profiling in Murine Models of Acute and Chronic Asthma: A Relationship with mRNAs Targets. PLOS ONE 6, e16509 (2011).

References cited herein are not an admission of prior art.

SUMMARY

This disclosure relates to the use of miRNA-483 (miR-483) and its target genes, UBE2C, pVHL and HIF1alpha, in managing the treatment of cardiovascular and inflammatory diseases. In certain embodiments this disclosure relates to pharmaceutical compositions comprising a miR-483 mimic and/or an HIF inhibitor and a pharmaceutically acceptable excipient for use in treating or preventing a vascular disease or condition. In certain embodiments, the miR-483 mimic is a double stranded nucleobase polymer or an expression vector that expresses mature human miR-483-5p and miR-483-3p sequences or operable fragments and variants.

In certain embodiments, this disclosure relates to the use of miR-483 to treat cardiovascular disease (CVD) or other disease of the heart or vasculature. Examples of such diseases include coronary artery diseases (CAD) such as angina and myocardial infarction or other CVDs including calcific aortic valve disease (CAVD), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

In certain embodiments, this disclosure relates to overexpressing the flow-sensitive miR-483 in vivo in any manner. In certain embodiments, this disclosure relates to silencing of HIF1alpha to treat cardiovascular disease (CVD) or other disease of the heart or vasculature. Examples of such diseases include coronary artery diseases (CAD) such as angina and myocardial infarction or other CVDs including calcific aortic valve disease (CAVD), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis. Examples of ways in which HIF1alpha may be silenced include administration of an inhibitor or blocker of HIF1alpha, but also may involve other approaches which knockdown HIF1alpha or block its function.

In certain embodiments, this disclosure relates to a miR-483 mimic which is a double stranded nucleobase polymer comprising, i) a human 5 prime mature guide strand miR-483 having 10 or more continuous nucleobases within 5'-AAGACGGGAGGAAAGAAGGGAG (SEQ ID NO: 1) and ii) a complementary passenger strand, wherein the complementary passenger strand is a single oligonucleotide comprising 10 or more continuous nucleobases within 5'-UCACUCCUCUCCUCCCGUCUU (SEQ ID NO: 2) or wherein the complementary passenger strand is two oligonucleotides that line up to form 10 or more continuous nucleobases within 5'-UCACUCCUCUCCUCCCGUCUU (SEQ ID NO: 2), wherein U is individually and independently at each occurrence optionally substituted with T.

In certain embodiments, the miR-483 mimic is a double stranded nucleobase polymer having a human 5 prime mature guide strand miR-483 consisting of 5'-AAGACGG-GAGGAAAGAAGGGAG (SEQ ID NO: 1) and having complementary passenger strand consisting of two oligonucleotides that line up to form 5'-UCACUCCUCUC-CUCCCGUCUU (SEQ ID NO: 2).

In certain embodiments, the double stranded nucleobase polymer comprises locked nucleobases. In certain embodiments, the locked nucleobases are in the two oligonucleotides of the complementary passenger strand.

In certain embodiments, this disclosure relates to nucleobase polymers disclosed herein 3' or 5' terminally conjugated to a polyphosphate, polyphosphate ester, trans-5'-vinylphosphonate, hydrocarbon, polyethylene glycol, saccharide, polysaccharide, cell penetrating peptide or combinations thereof. Typically, the cell penetrating peptide is a positively charged peptide, arginine-rich peptide, oligoarginine peptide (7-12), or octa-arginine (R8).

In certain embodiments, this disclosure relates to methods of treating or preventing a vascular disease or condition comprising administering an effective amount of a pharmaceutical composition comprising miR-483 mimic disclosed herein to a subject in need thereof. In certain embodiments, the subject is at risk of, exhibiting symptoms of, or diagnosed with a calcific aortic valve disease (CAVD), atherosclerosis, myocardial infarction, stroke, congestive heart failure, or arrhythmia. In certain embodiments, the miR-483 mimic is administered in combination with a statin such as atorvastatin, pravastatin, cerivastatin, lovastatin, mevastatin, pitavastatin, rosuvastatin, simvastatin, fluvastatin, or combinations thereof.

In certain embodiments, this disclosure relates to methods of treating or preventing a vascular disease or condition comprising administering an effective amount of a pharmaceutical composition comprising HIF1alpha pathway inhibitor to a subject in need thereof. In certain embodiments, the HIF1alpha pathway inhibitor is S-2-amino-3-[4'-N,N,-bis (chloroethyl)amino]phenyl propionic acid N-oxide or salt thereof. In certain embodiments, the HIF1alpha pathway inhibitor is administered in combination with a statin such as, pravastatin, cerivastatin, lovastatin, mevastatin, pitavastatin, rosuvastatin, simvastatin, fluvastatin, or combinations thereof.

In certain embodiments, this disclosure relates to pharmaceutical compositions comprising expression vectors of disclosed herein and a pharmaceutically acceptable excipient.

In certain embodiments, this disclosure relates to method of treating or preventing a vascular disease or condition comprising administering an effective amount of a pharmaceutical composition comprising an expression vector disclosed herein to a subject in need thereof.

In certain embodiments, the disclosure relates to particles comprising a cyclodextrin polymer or a particle with a lipid, or hydrophilic membrane and ionizable or cationic core comprising a nucleobase polymer disclosed herein.

In certain embodiments, this disclosure relates to pharmaceutical compositions comprising the nucleobase polymer disclosed herein or a particle comprising a nucleobase polymer disclosed herein, and a pharmaceutically acceptable excipient.

In certain embodiments, the disclosure relates to methods of treating or preventing a vascular disease or condition comprising administering an effective amount of a pharmaceutical composition disclosed herein to a subject in need thereof.

In certain embodiments, the subject is a human that is at risk of, exhibiting symptoms of, or diagnosed with atherosclerosis, aneurysm, peripheral vascular disease, coronary heart disease, heart failure, right ventricular hypertrophy, cardiac dysrhythmia, endocarditis, inflammatory cardiomegaly, myocarditis, vascular heart disease, stroke, cerebrovascular disease, or peripheral arterial disease.

In certain embodiments, the disclosure relates to pharmaceutical composition comprising the nucleobase polymer or RNA disclosed herein or a particle comprising nucleobase polymer or RNA disclosed herein, and a pharmaceutically acceptable excipient.

In certain embodiments, the disclosure relates to methods of treating or preventing a vascular disease condition comprising administering an effective amount of a pharmaceutical composition comprising the nucleobase polymer or RNA disclosed herein or a particle comprising the nucleobase polymer or RNA disclosed herein.

In certain embodiments, the disclosure relates to medical devices, such as stents, e.g., mesh tube comprising compositions disclosed herein, e.g., miR-483 or miR-483 mimic or their derivatives, HIF inhibitors, and/or RNA interference therapeutic compositions.

In certain embodiments, the disclosure relates to vascular or non-vascular medical device coated or conjugated with a nucleobase polymer or HIF inhibitors disclosed herein. In certain embodiments, the nucleobase polymers are linked to polymers on the surface of the device. In certain embodiments, the nucleobase polymer is integrated to release with biodegradable polymer. In certain embodiments, medical device is selected from a stents, pace maker, guide wire, delivery balloon, catheter, bioresorbable vascular scaffold, embolic protection device.

In certain embodiments, the disclosure relates to a gene therapy using a vector that expresses human miR-483 to knockdown UBE2C in human cells. In certain embodiments, the disclosure relates to a gene therapy using a vector that expresses siRNA to knockdown UBE2C mRNA in human cells.

BRIEF DESCRIPTION OF THE DRAWINGS

FIG. 3B shows images of HAVECs sheared for 72 hours by LS or OS and immunostained with antibodies for pVHL or HIF1alpha.

FIG. 3C shows quantification data of FIG. 3B.

FIG. 3D shows data of expression of pVHL and HIF1Alpha in HAVECS exposed to LS or OS qPCR normalized to 18S.

FIG. 3E show data where HAVECs were treated with siCtrl or siUBE2C for 24 hours, followed by exposure to OS for 24 hours and protein expression of pVHL was measured by Western blot.

FIG. 3F shows quantification data of FIG. 3E.

FIG. 3G shows images in a HIF1alpha study, where HAVECs were treated with SiUbe2c or SiCtrl and exposed to OS for 72 hour and were immunostained with the HIF1alpha.

FIG. 3H shows quantification data of FIG. 3G.

DETAILED DESCRIPTOIN

Figure 1A:
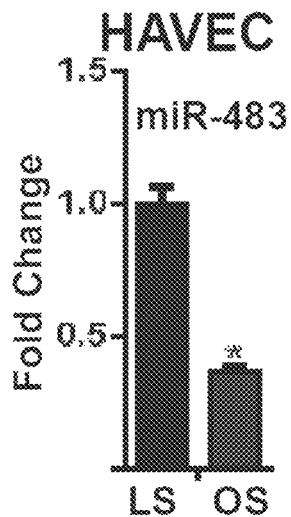
FIG. 1A shows data indicating miR-483 expression is shear-sensitive and side-specific in ECs. qPCR was performed using RNAs from HAVECs exposed to unidirectional laminar (LS) or oscillatory (OS) shear for 24 hr.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, immunology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

"Subject" refers any animal, preferably a human patient, livestock, rodent, monkey or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

A "nucleic acid," or "oligonucleotide," is defined as a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide can be, for example, ribose sugars (a "ribonucleic acid," or "RNA"), or deoxyribose sugars (a "deoxyribonucleic acid," or "DNA"). In some cases, the polymer can comprise both ribose and deoxyribose sugars. Examples of bases include, but not limited to, the naturally-occurring bases (e.g., adenosine or "A," thymidine or "T," guanosine or "G," cytidine or "C," or uridine or "U"). In some cases, the polymer can also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'- deoxyuridine, 3-nitorpyrrole, 4-methylindole, 4-thiouridine, 4-thiothymidine, 2- aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, $N^1$-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, 6-O-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide can include DNA, RNA, modified DNA, modified RNA, antisense oligonucleotides, expression plasmid systems, nucleotides, modified nucleotides, nucleosides, modified nucleosides, intact genes, or combinations thereof. Other examples of polynucleotides include interfering RNA, natural or unnatural siRNAs, shRNAs, microRNAs, ribozymes, DNA plasmids, antisense oligonucleotides, randomized oligonucleotides, or ribozymes. A nucleic acid sequence may be composed of DNA nucleotides, RNA nucleotides or a combination of both types and may include natural nucleotides, chemically modified nucleotides and synthetic nucleotides.

Disturbed Flow Increases UBE2C in Endothelial Cells via Loss of miR-483-3p, Inducing Aortic Valve Calcification by the HIF1alpha Pathway Calcific aortic valve disease (CAVD), characterized by AV sclerosis and calcification, is a major cause of death in the aging population. AV calcification occurs preferentially on the fibrosa-side exposed to disturbed and oscillatory flow conditions (OS) compared to the ventricularis-side exposed to stable and laminar flow conditions (LS) by unclear mechanisms. It was discovered that the ubiquitin E2 ligase-C (UBE2C) was upregulated by OS and decreased by LS. OS-induced endothelial inflammation.

Endothelial to mesenchymal transition (EndMT) is a biological process involved in tissue development, regeneration, and disease progression, controlled by signaling networks including microRNAs (miRNAs). See Kim, BMB Rep. 2018, 51(2): 65-72. During endothelial to mesenchymal transition (EndMT), endothelial cells (ECs) undergo cellular phenotypic switching due to environmental cues losing their endothelial characteristics and displaying mesenchymal phenotypes characterized by being invasive and migratory. For example, ECs lose their ability to express endothelial markers, such as vascular endothelial cadherin (VE-cadherin), and gain expression of mesenchymal markers such as alpha smooth muscle actin (alpha-SMA).

Endothelial-mesenchymal transition (EndMT) was mediated by UBE2C in HAVECs. Although it is not intended that embodiments of this disclosure be limited by any particular mechanism, a possible mechanism by which UBE2C increased HIF1alpha levels was by ubiquitination and degradation of its upstream regulator pVHL in HAVECs exposed to OS. In vitro findings were corroborated by increased immunostaining of UBE2C, HIF1alpha, and markers of inflammation (VCAM1), EndMT (TWIST1) and AV calcification (RUNX2) in the fibrosa-side, while pVHL was overexpressed in the ventricularis-side of human AV leaflets. Additionally, reduction of miR-483-3p (miR-483) by OS led to UBE2C expression in HAVECs. A miR-483 mimic protected against endothelial inflammation and EndMT in HAVECs and AV calcification ex vivo by downregulating UBE2C. Moreover, treatment with the HIF1alpha inhibitor (PX478) significantly reduced porcine AV calcification ex vivo in static and OS conditions. These results suggest that miR-483 and UBE2C are shear-sensitive anti- and pro-CAVD molecules, respectively, that regulate the HIF1alpha pathway. The miR-483 mimic and HIF1alpha pathway inhibitors have therapeutic applications for CAVD.

MicroRNA-483 (miR-483) is a shear-sensitive and side-dependent miRNA that regulates endothelial inflammation and EndMT by targeting UBE2C, which in turn regulates pVHL and HIF1alpha under normal atmospheric conditions, ultimately leading to AV calcification. A miR-483 mimic as well as the HIF1alpha inhibitor PX478 effectively reduced AV calcification of porcine AVs ex vivo.

MicroRNA-483 expression is increased by LS and in the ventricularis side which is exposed to s-flow, while decreased by OS and in the fibrosa side which is exposed to d-flow. Most shear experiments were carried out in this study by using the simple LS and OS profile to represent the more complex ventricularis and fibrosa flow profiles, respectively. Fortunately, HAVECs responded to the ventricularis and fibrosa flow profiles in a similar manner to the LS and OS conditions. MicroRNA-483 potently regulates endothelial function by protecting against inflammation, proliferation, and EndMT. Recent data showed that miR-483 mediates EndMT by targeting CTGF in human umbilical vein ECs. Angiotensin II was shown to inhibit expression of miR-483 targeting the renin-angiotensin system genes in smooth muscles and heart. These genes including CTGF, however, were not shear sensitive in a gene array study using HAVECs and porcine AVs. MicroRNA-483 is located in the intronic region of insulin-like growth factor 2 (IGF2), and is reported to be mediated by KLF. Similarly, expression of miR-483 and IGF2 are mediated in a KLF2-dependent manner in HAVECs.

UBE2C and ASH2L were identified as two shear-sensitive targets of miR-483 through in silico and validation studies. ASH2L is a member of the COMPASS complex responsible for histone 3 lysine 4 tri-methylation, an important epigenetic modification that induces expression of numerous genes. ASH2L may plays a role in epigenetic modification of endothelial function and CAVD. UBE2C alone plays a role in regulation of inflammation and EndMT. UBE2C is a member of the APC/C and is reported to catalyze the initial mono-ubiquitination of protein substrates such as cyclins. Once cyclins are mono-ubiquitinated, another E2 ligase, Ube2s, then elongates the ubiquitin chain (poly-ubiquitination) leading to their proteasomal degradation. Interestingly, pVHL is another substrate of both APC/C and Ube2s, but it was unknown whether UBE2C regulates pVHL ubiquitination. Additionally, OS was shown to stabilize HIF1alpha expression under normal atmospheric conditions in vascular endothelial cells by activating NF-KB and inducing expression of the deubiquitinating enzyme Cezanne; however, it was unknown whether pVHL is regulated by shear stress and regulates HIF1alpha expression under flow conditions. It was discovered that pVHL is highly shear-sensitive, losing its expression in OS in HAVECs and in the fibrosa side exposed to d-flow in a UBE2C-dependent manner. Conversely, OS increased HIF1alpha expression in a UBE2C-dependent manner in HAVECs and in the fibrosa side. These findings suggest that UBE2C regulates pVHL and HIF1alpha expression in HAVECs. Although there is an increase in HIF1alpha expression under OS condition, it is interesting to note that siRNA-mediated knockdown of UBE2C is able to significantly reduce the HIF1alpha expression by post-translational pVHL-mediated degradation preventing the downstream HIF1alpha signaling cascade.

UBE2C targets pVHL by binding and mediating its degradation in a ubiquitination-dependent manner. Further, data using the pVHL ubiquitination site mutants indicates that binding of UBE2C to pVHL is independent of the ubiquitination sites on pVHL; however, the UBE2C-dependent degradation of pVHL requires at least one of its ubiquitination sites. The degradation of pVHL further led to increased stabilization of HIF1alpha, which in turn induced endothelial inflammation, EndMT and AV calcification.

HIF1alpha-pathway and miR-483 are potential therapeutic targets for CAVD. Treatment with the miR-483 mimic or the HIF1alpha inhibitor PX478 significantly reduced AV calcification of porcine AVs in static and sheared conditions demonstrating their potential as anti-CAVD therapeutics. Notably, numerous clinical trials are underway using various HIF1alpha inhibitors for cancer treatment. Experiments herein using PX478 demonstrates the potential of repurposing some of these FDA-approved HIF1alpha drugs to prevent and treat CAVD. The miR-483-dependent UBE2C/pVHL/HIF1alpha pathway established based on the in vitro studies is relevant under in vivo conditions as well, where AVs are exposed to multiple mechanical forces such as pressure and stretch in addition to shear stress.

Nucleobase Polymer Therapeutics

The term "nucleobase polymer" refers to a polymer comprising nitrogen containing aromatic or heterocyclic bases that bind to naturally occurring nucleic acids through hydrogen bonding otherwise known as base pairing. A typical nucleobase polymer is a nucleic acid, RNA, DNA, or chemically modified form thereof. A nucleic acid may be single or double stranded or both, e.g., they may contain overhangs. Nucleobase polymers may contain naturally occurring or synthetically modified bases and backbones. In certain embodiments, a nucleobase polymer need not be entirely complementary, e.g., may contain one or more insertions, deletions, or be in a hairpin structure provided that there is sufficient selective binding. In certain embodiments, the disclosure relates to composition comprising an isolated antisense nucleobase polymers, interference nucleobase polymers and RNA-blocking oligonucleotides.

In certain embodiments, the disclosure relates to compositions comprising locked nucleobase polymers that mimic miR-483. As used herein, a "locked nucleobase" or "locked nucleobase polymers" (LNPs) refer to nucleobases and nucleobase polymers that contain bicyclic monomers. Nucleic acid are conformationally locked when the ribose ring is connected by a methylene bridge (blue) between the 2'-O and 4'-C atoms; thus, "locking" the ribose ring to form a dioxabicyclic rings. Locked nucleobase polymers may consist of a mixture of locked nucleobases and unlocked nucleobases, e.g., with ribose ring(s) that are not bicyclic as in naturally occurring nucleic acids. Inserting bicyclic monomers into a nucleobase polymer alters interactions with naturally occurring enzymes that degrade oligonucleotides. Thus, by altering nucleobase polymers to contain locked and unlocked nucleobases one may prevent natural enzymes, such as RNase H1, from cleaving the nucleobase polymer hybridized to naturally occurring RNA or DNA. LNPs may also contain a phosphorothioate-modified backbone, partially or fully, which further prevents degradation.

In another embodiment, nucleobase polymers include one or more (e.g., about 1, 2, 3, 4, 5, 6, 7, 8, 9, 10, or more)

"locked" nucleotides such as 2',4'-C methylene bicyclo nucleotides and 2'-O,4'-C-aminomethylene bridged nucleotides) (see for example U.S. Pat. No. 6,639,059, U.S. Pat. No. 6,670,461, U.S. Pat. No. 7,053,207, and U.S. Pat. No. 7,427,672).

MicroRNA (miRNA) mimics are chemically modified double-stranded RNAs that mimic endogenous miRNAs and enable miRNA functional analysis by up-regulation of miRNA activity. miRNA mimics typically contain chemical modifications such a phosphorothioate (PS) backbone in the minor (passanger) strand, designed 3p.

Anti-miRNA inhibitors are modified single-stranded RNA molecules designed to specifically bind to and inhibit endogenous RNA molecules. Mature microRNAs are typically around 20 nucleotides in length, which means that even full length traditional antisense inhibitors (such as 2'-O-Me) may have limited affinity for their microRNA targets that are rich in AT nucleotides. Incorporating monomers that are conformational locked into the microRNA inhibitors increases the affinity of the inhibitors for target microRNAs. In certain embodiments, blocking locked nucleobase polymers disclosed herein are 8 to 25 or 12 to 15 nucleobases.

Many nucleobase polymers differ from native RNA or DNA in the chemical structure that links the four common bases. For example, a RNA may be modified to contain phosphorothioates instead of phosphodiester linkages. Nucleobase polymers that contain phosphorothioates may hybridize to RNA and reduce RNase H mediated degradation.

In certain embodiments, nucleobase polymers are contemplated to comprise peptide nucleic acids (PNAs). One example of a peptide nucleic acid is one that has 2-aminoethyl glycine linkages or similar analogues in place of the regular phosphodiester backbone. Other examples include d-lysPNA, argPNA, alternating units of 2-aminocyclopentanoic acid and pyrrolidine-2-carboxylic acid (pyrPNA). See Nielson, Chem & Biodiversity, 2010, 7:786.

In certain embodiments, nucleobase polymers are contemplated to comprise non-natural nucleobases such as, but not limited to, pseudoisocytosine as a substitute for cytosine, diaminopurine as a substitute for adenine, bicyclic thymine analogue (7Cl-bT), thiouracil, or combinations thereof. With regard to any of the sequences disclosed herein, any U is individually and independently at each occurrence uracil (U) or thymine (T). With regard to any of the sequences disclosed herein, any T is individually and independently at each occurrence uracil (U) or thymine (T).

In certain embodiments, nucleobase polymers are contemplated to comprise phosphorodiamidate morpholino oligomers (PMO). In certain embodiments, the nucleobase polymer comprises monomers of (2-(hydroxymethyl)morpholino)(piperazin-1-yl)phosphinate. In certain embodiments, the disclosure contemplates chemical conjugation of PMO to arginine-rich, polyarginine, or cell penetrating peptides (CPP) such as $(R-Ahx-R)_4$ (with Ahx standing for 6-aminohexanoyl). CPPs may be conjugated to the 3' end of the PMO or to the 5' end or both. See Warren & Bavari, Antiviral Research, 2012, 94(1):80-88 and Betts et al., Molecular Therapy Nucleic Acids, 2012, 1: e38.

Processing of human miR-483 results in mature double stranded complex for which the 5' sequence (hsa-miR-483-5p) of 5'-AAGACGGGAGGAAAGAAGGGAG (SEQ ID NO: 1), which hybridizes to the 3' sequence (hsa-miR-483-3p) 5'-UCACUCCUCUCCUCCCGUCUU (SEQ ID NO: 2).

In certain embodiments, the disclosure relates to compounds, compositions, and methods useful for modulating of miR-483 using nucleobase polymers. In particular, the instant disclosure features small nucleic acid molecules, such as short interfering short interfering RNA (siRNA), double-stranded RNA (dsRNA), micro-RNA (miRNA), and short hairpin RNA (shRNA) molecules.

LNP miRNA target site blockers (TSBs) are antisense oligonucleotides designed to compete with miRNA/RISC for a miRNA target site of a particular mRNA. When introduced into cells, a target site blocker will mask the miRNA target site by hybridizing strongly with it, effectively preventing the miRNA from interacting with the specific target microRNA at that location of the mRNA, without otherwise affecting the activity of the endogenous miRNA at other locations.

RNA interference refers to the process of sequence specific post-transcriptional gene silencing in animals mediated by short interfering nucleobase polymers sometimes referred to as post-transcriptional gene silencing or RNA silencing. The presence of long dsRNAs in cells is thought to stimulate the activity of a ribonuclease III enzyme referred to as Dicer. Dicer is thought to be involved in the processing of the dsRNA into short pieces of dsRNA known as short interfering RNAs (siRNAs). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control. The RNAi response is thought to feature an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex. In addition, RNA interference involves s RNA (e.g., microRNA or miRNA) mediated gene silencing. As such, siRNA molecules can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Elbashir et al., 2001, Nature, 411, 494, describe RNAi induced by introduction of duplexes of synthetic 21-nucleotide RNAs in cultured mammalian cells including human embryonic kidney and HeLa cells. Work in Drosophila embryonic lysates has revealed certain preferences for siRNA length, structure, chemical composition, and sequence that mediate efficient RNAi activity. These studies have shown that 21 nucleotide siRNA duplexes are typical when using two 2-nucleotide 3'-terminal nucleotide overhangs. Substitution of 3'-terminal siRNA nucleotides with deoxy nucleotides was shown to be tolerated. Other studies have indicated that a 5'-phosphate on the target-complementary strand of a siRNA duplex is beneficial for siRNA activity and that ATP is utilized to maintain the 5'-phosphate moiety on the siRNA. siRNA molecules lacking a 5'-phosphate are active when introduced exogenously.

In certain embodiments, this disclosure contemplates an expression vector encoding a nucleic acid encoding miR-483. The expression vector is introduced into cells. Following the vector gene transcription, the overexpressed miR-483 is processed and acts to inhibit inflammation or calcium formation.

A nucleobase polymer can be synthetic or recombinantly produced nucleic acid, unmodified or chemically-modified, compared to naturally occurring nucleic acids. A nucleic acid can be chemically synthesized, expressed from a vector or enzymatically synthesized. Various chemically-modified, synthetic short interfering nucleic acid (siNA) molecules are capable of modulating UBE2C activity in cells by RNA interference (RNAi).

In one embodiment, the disclosure relates to a double-stranded short interfering nucleobase polymers that down-regulates UBE2C or expression of UBE2C, wherein said nucleobase polymer comprises about 15 to about 35 base pairs.

In certain embodiments, the nucleobase polymer or interference nucleic acid is in a hairpin.

In some embodiments, the disclosure relates to methods of treating a subject diagnosed with a vascular condition by administering a pharmaceutical composition with a nucleobase polymer or nucleic acid that is a single strand.

In certain embodiments, this disclosure relates to particles comprising a hydrophilic or lipid membrane and ionizable or cationic core comprising the nucleobase polymer. Siegwart et al. report the synthesis of core shell nanoparticles by the reaction of epoxide-containing block copolymers with polyethylene glycol monomers and amines. See PNSA, 2011, 108(32):12996-3001.

In certain embodiments, contemplated particles comprise block copolymers of poly(d,l-lactide) (PLA) or poly(d,l-lactide-co-glycolide) (PLGA) and poly(ethylene glycol) (PEG), in which nucleobase polymers were physically entrapped without chemical modification.

In certain embodiments, contemplated particles comprise a hydrophobic biodegradable polymeric core that allows for the encapsulation and controlled release of nucleobase polymers, a hydrophilic shell that protects the nucleobase polymers, and optionally a targeting ligand that mediated molecular interactions between particle and target endothelial cells.

In certain embodiments, contemplated particles comprise a linear polymer in which positively or negatively charged groups alternate with polysaccharides (e.g., cyclodextrin). Upon mixing with nucleobase polymers, the positively or negatively charged polymer respectively associates with the negatively or positively charged backbone of nucleobase polymers, nucleic acids, or RNAs. Several polymer/complexes self-assemble into a nanoparticle that fully protects the molecules from degradation in serum. Formation of inclusion complexes between adamantane (AD) and β-cyclodextrin allows noncovalent incorporation of stabilizing (via PEG-AD conjugates) and/or targeting (via ligand-PEG-AD conjugates) components to polymer-nucleic acid nanoparticles. See Suzie & Davis, Bioconjugate Chemistry, 2002, 13(3):630-639. Directly conjugating the nucleobase polymer to a cyclodextrin-based polymer is also contemplated. See Heidel & Schluep, "Cyclodextrin-Containing Polymers: Versatile Platforms of Drug Delivery Materials," J Drug Delivery, 2012, Article ID 262731, 17 pages.

In certain embodiments, the disclosure relates to a nucleobase polymers disclosed herein optionally conjugated to a detectable marker or label such as, but not limited to, a fluorescent dye, radio isotope, stable isotopes with lower natural abundance, positron-emitting radionuclide (tracer), antibody epitope, biotin, ligand, steroid, quantum dot. Useful physical properties include a characteristic electromagnetic spectral property such as emission or absorbance, magnetism, electron spin resonance, electrical capacitance, dielectric constant or electrical conductivity. The marker may be ferromagnetic, paramagnetic, diamagnetic, luminescent, electrochemiluminescent, fluorescent, phosphorescent, chromatic or have a distinctive mass. Fluorescent moieties that are useful as markers include dansyl fluorophores, coumarins and coumarin derivatives, fluorescent acridinium moieties and benzopyrene based fluorophores and quantum dots. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity, positron emission tomography, and nuclear magnetic resonances and use of a mass spectrometer to detect presence of a marker with a specific molecular mass.

Synthesis of Nucleobases Polymers

Small nucleobase polymers and nucleic acid motifs ("small" refers to nucleic acid motifs no more than 100 nucleotides in length, preferably no more than 80 nucleotides in length, and most preferably no more than 50 nucleotides in length; e.g., individual oligonucleotide sequences or sequences synthesized in tandem) are preferably used for exogenous delivery. Exemplary molecules of the instant disclosure are chemically synthesized, and others can similarly be synthesized.

One synthesizes oligonucleotides (e.g., certain modified oligonucleotides or portions of oligonucleotides) using protocols known in the art as, for example, described in U.S. Pat. No. 6,001,311. The synthesis of oligonucleotides makes use of common nucleic acid protecting and coupling groups, such as dimethoxytrityl at the 5'-end and phosphoramidites at the 3'-end. In a non-limiting example, small scale syntheses are conducted on a 394 Applied Biosystems, Inc. synthesizer using a 0.2 micro mol scale protocol with a 2.5 min coupling step for 2'-O-methylated nucleotides and a 45 second coupling step for 2'-deoxy nucleotides or 2'-deoxy-2'-fluoro nucleotides. Alternatively, syntheses at the 0.2 micro mol scale can be performed on a 96-well plate synthesizer. A 33-fold excess of 2'-O-methyl phosphoramidite and a $10^5$-fold excess of S-ethyl tetrazole can be used in each coupling cycle of 2'-O-methyl residues relative to polymer-bound 5'-hydroxyl. A 22-fold excess of deoxy phosphoramidite and a 70-fold excess of S-ethyl tetrazole mop can be used in each coupling cycle of deoxy residues relative to polymer-bound 5'-hydroxyl. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF; and oxidation solution is 16.9 mM $I_2$, 49 mM pyridine, 9% water in THF. S-Ethyl tetrazole solution (0.25 M in acetonitrile) is made up from the solid obtained from American International Chemical, Inc. Alternately, for the introduction of phosphorothioate linkages, Beaucage reagent (3H-1,2-benzodithiol-3-one 1,1-dioxide, 0.05 M in acetonitrile) is used.

Deprotection of the DNA-based oligonucleotides is performed as follows: the polymer-bound trityl-on oligonucleotide is transferred to a 4 mL glass screw top vial and suspended in a solution of 40% aqueous methylamine (1 mL) at 65 degrees for 10 minutes. After cooling to −20 degrees, the supernatant is removed from the polymer support. The support is washed three times with 1.0 mL of EtOH:MeCN:HO/3:1:1, vortexed and the supernatant is then added to the first supernatant. The combined supernatants, containing the oligonucleotide, are dried.

Alternatively, the nucleic acid molecules can be synthesized separately and joined together post-synthetically, for example, by ligation or by hybridization following synthesis and/or deprotection.

Nucleic acids can also be assembled from two distinct nucleic acid strands or fragments wherein one fragment includes the sense region and the second fragment includes the antisense region of the RNA molecule.

The nucleic acid molecules can be modified extensively to enhance stability by modification with nuclease resistant groups, for example, 2'-amino, 2'-C-allyl, 2'-fluoro, 2'-O-methyl, 2'-H). Constructs can be purified by gel electrophoresis using general methods or can be purified by high-pressure liquid chromatography and re-suspended in water.

Chemically synthesizing nucleic acid molecules with modifications (base, sugar and/or phosphate) can prevent their degradation by serum ribonucleases, which can increase their potency. See e.g., U.S. Pat. No. 5,652,094, U.S. Pat. No. 5,334,711, and U.S. Pat. No. 6,300,074. All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

In one embodiment, nucleic acid molecules include one or more (e.g., about 1, 2, 3, 4, 5, 6, 7, 8, 9, 10, or more) G-clamp nucleotides. A G-clamp is a tricyclic aminoethyl-phenoxazine 2'-deoxycytidine or analogue. See Lin &. Matteucci, J Am Chem Soc, 1998, 120, 8531-8532; Flanagan, et al., Proc Nat Acad Sci USA, 1999, 96, 3513-3518; and Maier, et al., Biochemistry, 2002, 41, 1323-1327. A single G-clamp analog substitution within an oligonucleotide can result in substantially enhanced helical thermal stability and mismatch discrimination when hybridized to complementary oligonucleotides. The inclusion of such nucleotides in nucleic acid molecules results in both enhanced affinity and specificity to nucleic acid targets, complementary sequences, or template strands.

In another embodiment, the disclosure features conjugates and/or complexes of nucleobase polymers. Such conjugates and/or complexes can be used to facilitate delivery of polymers into a biological system, such as a cell. Contemplated conjugates include those with cell penetrating peptide. The conjugates and complexes provided may impart therapeutic activity by transferring therapeutic compounds across cellular membranes, altering the pharmacokinetics, and/or modulating the localization of nucleic acid molecules. In general, the transporters described are designed to be used either individually or as part of a multi-component system, with or without degradable linkers. These compounds improve delivery and/or localization of nucleic acid molecules into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

In yet another embodiment, nucleobase polymers having chemical modifications that maintain or enhance enzymatic activity of proteins involved in RNAi are provided. Such nucleic acids are also generally more resistant to nucleases than unmodified nucleic acids. Thus, in vitro and/or in vivo the activity should not be significantly lowered.

In another aspect a nucleobase polymer comprises one or more 5' and/or a 3'-cap structure, for example on only the sense strand, the antisense strand, or both strands.

A "cap structure" refers to chemical modifications, which have been incorporated at either terminus of the oligonucleotide. See, for example, Adamic et al., U.S. Pat. No. 5,998,203. These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, Tetrahedron 49, 1925).

In one embodiment, the disclosure features modified nucleobase polymer, with phosphate backbone modifications comprising one or more phosphorothioate, phosphorodithioate, methylphosphonate, phosphotriester, morpholino, carboxymethyl, acetamidate, polyamide, sulfonate, sulfonamide, sulfamate, formacetal, thioformacetal, and/or alkylsilyl, substitutions.

Pharmaceutical Compositions

The following protocols can be utilized for the delivery of nucleobase polymers. A nucleobase polymer can be adapted for use to prevent or treat a vascular disease or condition that is related to or will respond to the levels of miR-483 or miR-483 mimic in the blood, a cell, or tissue, alone or in combination with other therapies. For example, a nucleobase polymer can be contained in a delivery vehicle, including liposomes, for administration to a subject, carriers and diluents and their salts, and/or can be present in pharmaceutically acceptable formulations. U.S. Pat. No. 6,395,713 and U.S. Pat. No. 5,616,490 further describe general methods for delivery of nucleic acid molecules. Nucleobase polymers can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example U.S. Pat. No. 7,141,540 and U.S. Pat. No. 7,060,498), poly(lactic-co-glycolic)acid (PLGA) and PLCA microspheres (see for example U.S. Pat. No. 6,447,796), biodegradable nanocapsules, and bioadhesive microspheres, or by proteinaceous vectors (U.S. Pat. No. 7,067,632). In another embodiment, the nucleobase polymers can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In one embodiment, a nucleobase polymer is complexed with membrane disruptive agents such as those described in U.S. Pat. No. 6,835,393. In another embodiment, the membrane disruptive agent or agents and nucleobase polymers are also complexed with a cationic lipid or helper lipid molecule, such as those lipids described in U.S. Pat. No. 6,235,310.

Embodiments of the disclosure feature a pharmaceutical composition comprising one or more nucleobase polymers in an acceptable carrier, such as a stabilizer, buffer, and the like. The nucleobase polymers or oligonucleotides can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions can also be formulated and used as tablets, capsules or elixirs for oral administration, suppositories for rectal administration, sterile solutions, suspensions for administration by injection, and the other compositions known in the art.

Embodiments of the disclosure also feature the use of the composition comprising surface-modified liposomes containing poly (ethylene glycol) lipids (PEG-modified, or long-circulating liposomes or stealth liposomes). These formulations offer a method for increasing the circulation and accumulation of in target tissues. The long-circulating liposomes enhance the pharmacokinetics and pharmacodynamics of DNA and RNA. See U.S. Pat. No. 5,820,873 and U.S. Pat. No. 5,753,613. Long-circulating liposomes are also likely to protect from nuclease degradation.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases, such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Methods of Use

This disclosure relates to the use of miRNA-483 and its target genes, UBE2C, pVHL and HIF1alpha, in managing the treatment of cardiovascular and inflammatory diseases. In certain embodiments this disclosure relates to pharmaceutical compositions comprising a miR-483 mimic and/or an HIF inhibitor and a pharmaceutically acceptable excipient for use in treating or preventing a vascular disease or condition. In certain embodiments, the miR-483 mimic is a double stranded nucleobase polymer or an expression vector that expresses mature human miR-483-5p and miR-483-3p sequences or operable fragments and variants.

In certain embodiments, this disclosure relates to the use of miR-483 to treat cardiovascular disease (CVD) or other disease of the heart or vasculature. Examples of such diseases include coronary artery diseases (CAD) such as angina and myocardial infarction or other CVDs including calcific aortic valve disease (CAVD), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

In certain embodiments, this disclosure relates to overexpressing the flow-sensitive miR-483 in vivo in any manner. In certain embodiments, this disclosure relates to silencing of HIF1alpha to treat cardiovascular disease (CVD) or other disease of the heart or vasculature. Examples of such diseases include coronary artery diseases (CAD) such as angina and myocardial infarction or other CVDs including calcific aortic valve disease (CAVD), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis. Examples of ways in which HIF1alpha may be silenced include administration of an inhibitor or blocker of HIF1alpha, but also may involve other approaches which knockdown HIF1alpha or block its function.

In certain embodiments, this disclosure relates to a miR-483 mimic is a double stranded nucleobase polymer comprising, i) a human 5 prime mature guide strand miR-483 having 10 or more continuous nucleobases within 5'-AAGACGGGAGGAAAGAAGGGAG (SEQ ID NO: 1) and ii) a complementary passenger strand, wherein the complementary passenger strand is a single oligonucleotide comprising 10 or more continuous nucleobases within 5'-UCACUCCUCUCCUCCCGUCUU (SEQ ID NO: 2) or wherein the complementary passenger strand is two oligonucleotides that line up to form 10 or more continuous nucleobases within 5'-UCACUCCUCUCCUCCCGUCUU (SEQ ID NO: 2), wherein U is individually and independently at each occurrence optionally substituted with T.

In certain embodiments, the miR-483 mimic is a double stranded nucleobase polymer having a human 5 prime mature guide strand miR-483 consisting of 5'-AAGACGGGAGGAAAGAAGGGAG (SEQ ID NO: 1) and having complementary passenger strand consisting of two oligonucleotides that line up to form 5'-UCACUCCUCUCCUCCCGUCUU (SEQ ID NO: 2).

In certain embodiments, the double stranded nucleobase polymer comprises locked nucleobases. In certain embodiments, the locked nucleobases are in the two oligonucleotides of the complementary passenger strand.

In certain embodiments, the miR-483 mimic is a double stranded nucleobase polymer comprising, i) a human 5 prime guide strand miR-483 having 5, 6, 7, 8, 9, 10, or more continuous nucleobases within 5'-AAGACGGGAGGAAAGAAGGGAG (SEQ ID NO: 1) and ii) a passenger strand having 5, 6, 7, 8, 9, 10, or more continuous nucleobases with 5'-UCACUCCUCUCCUCCCGUCUU(SEQ ID NO: 2), wherein U is individually and independently at each occurrence optionally substituted with T.

In certain embodiments, it is contemplated the passenger strand is a mixture of two, three, or more oligonucleotides, wherein the multiple oligonucleotide together hybridize to the guide strand. In certain embodiments, two passenger strands when lined up from the 5' to the 3' direction form a continuous sequence that resembles 5'-UCACUCCUCUCCUCCCGUCUU (SEQ ID NO: 2) or fragment thereof, which hybridizes to the guide strand. For example, 5'-UCACUCCUCUC (SEQ ID NO: 4) and 5'-CUCCCGUCUU (SEQ ID NO: 5).

In certain embodiments, it is contemplated the guide strand is a mixture of two, three, or more oligonucleotides, wherein the multiple oligonucleotide together hybridize to the passenger strand. In certain embodiments, two guide strands when lined up from the 5' to the 3' direction form a continuous sequence that resembles 5'-AAGACGGGAGGAAAGAAGGGAG (SEQ ID NO: 1) or fragment thereof, which hybridizes to the passenger strand. For example, 5'-AAGACGGGAGG (SEQ ID NO: 6) and 5'-AAAGAAGGGAG (SEQ ID NO: 7).

In certain embodiments, it is contemplated the guide strand is a mixture of two, three, or more oligonucleotides and the passenger strand is a mixture of two, three, or more oligonucleotides, wherein the multiple oligonucleotide of the guide strand together hybridize to the multiple oligonucleotides of the passenger strand. For example, the guide strand may be a combination of 5'-AAGACG (SEQ ID NO: 8) and GGAGGAAAGAAGGGAG (SEQ ID NO: 9) and the passenger strand by be a combination of 5'-UCACUC (SEQ ID NO: 10) and CUCUCCUCCCGUCUU (SEQ ID NO: 11). In certain embodiments, it is contemplated the passenger strand comprises locked nucleobases. In certain embodiments, it is contemplated the guide strand comprises locked nucleobases.

In certain embodiments, the double stranded nucleobase polymer comprises a locked nucleobase. In certain embodiments, a locked nucleobase is in a passenger strand. In certain embodiments, a locked nucleobase is in the human 5 prime mature guide strand.

In certain embodiments, the nucleobase polymer or the passenger strand or guide strand comprises monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, 1-(hydroxymethyl)-2,5-dioxabicyclo[2.2.1]heptan-7-yl phosphate, O-(1-(hydroxymethyl)-2,5-dioxabicyclo[2.2.1]heptan-7-yl) phosphorothioate, 5-(hydroxymethyl)-2,6-dioxa-3-azabicyclo[3.2.1]octan-8-ol, 5-(hydroxymethyl)-2,6-dixa-3-azabicyclo[3.2.1]octan-8-yl phosphate, O-(5-(hydroxymethyl)-2,6-dioxa-3-azabicyclo[3.2.1]octan-8-yl) phosphorothioate, P-(2-(hydroxymethyl)morpholino)-N,N-dimethylphosphoramidate, morpholin-2-ylmethanol, (2-(hydroxymethyl)morpholino) (piperazin-1-yl)phosphinate, or peptide nucleic acids or combinations thereof.

In certain embodiments, the human 5 prime mature guide strand miR-483 is not greater than 15, 20, 25, or 30 nucleobases. In certain embodiments, the passenger strand is not greater than 15, 20, 25, 30 nucleobases. In certain embodiments, the double stranded nucleobase polymer does not contain more than 30, 40, 50, or 60, nucleobases counting all of the nucleobases within both the human 5 prime mature guide strand miR-483 and the passenger strand(s).

In certain embodiments, a nucleobase polymer disclosed herein is 3' or 5' terminally conjugated to a polyphosphate, polyphosphate ester, trans-5'-vinylphosphonate, hydrocarbon, polyethylene glycol, saccharide, polysaccharide, cell penetrating peptide or combinations thereof. Typically, the cell penetrating peptide is a positively charged peptide, arginine-rich peptide, oligoarginine peptide (7-12), or octaarginine (R8).

In certain embodiments, this disclosure relates to methods of treating or preventing a vascular disease or condition comprising administering an effective amount of a pharmaceutical composition comprising miR-483 mimic disclosed herein to a subject in need thereof. In certain embodiments, the subject is at risk of, exhibiting symptoms of, or diagnosed with a calcific aortic valve disease (CAVD), atherosclerosis, myocardial infarction, stroke, congestive heart failure, or arrhythmia. In certain embodiments, the miR-483 mimic is administered in combination with a statin such as atorvastatin, pravastatin, cerivastatin, lovastatin, mevastatin, pitavastatin, rosuvastatin, simvastatin, fluvastatin, or combinations thereof.

In certain embodiments, this disclosure relates to methods of treating or preventing a vascular disease or condition comprising administering an effective amount of a pharmaceutical composition comprising HIF1alpha pathway inhibitor to a subject in need thereof. In certain embodiments, the HIF1alpha pathway inhibitor is S-2-amino-3-[4'-N,N,-bis(chloroethyl)amino]phenyl propionic acid N-oxide (PX478) or salt thereof. In certain embodiments, the HIF1alpha pathway inhibitor is roxadustat, vadadustat, daprodustat, molidustat, Lificiguat (YC-1), 2-Methoxyestradiol (2-MeOE2), N-(methoxyoxoacetyl)-glycine methyl ester, methyl 3-[[2-[4-(2-adamantyl)phenoxy]acetyl]amino]-4-hydroxybenzoate, Dimethyl-bisphenol A, Chrysin, Chetomin, 1-cyclopropyl-4-[4-[[5-methyl-3-[3-[4-(trifluoromethoxy)phenyl]-1,2,4-oxadiazol-5-yl]-1H-pyrazol-1-yl]methyl]-2-pyridinyl]-piperazine (BAY 87-2243), N,N'-(disulfanediyl-bis(ethane-2,1-diyl))bis(2,5-dichlorobenzenesulfonamide) (KC7F2), N-[[1,2-Dihydro-4-hydroxy-2-oxo-1-(phenylmethyl)-3-quinolinyl]carbonyl]glycine (IOX2), methyl 3-(2-(4-(adamantan-1-yl)phenoxy)acetamido)-4-hydroxybenzoate (LW6), 5-[5-Methyl-1-(4-methyl-benzyl)-1H-pyrazol-3-yl]-3-(4-trifluoromethoxy-phenyl)-[1,2,4]oxadiazole (HIFIN33), 3,4-dimethoxy-N-[(2,2-dimethyl-2H-chromen-6-yl)methyl]-N-phenylbenzenesulfonamide (KCN1), or salts thereof. In certain embodiments, the HIF1alpha pathway inhibitor is administered in combination with a statin such as, pravastatin, cerivastatin, lovastatin, mevastatin, pitavastatin, rosuvastatin, simvastatin, fluvastatin, or combinations thereof.

In certain embodiments, this disclosure relates to an expression vector that encodes a single nucleic acid stem loop sequence in operable combination with a heterologous promoter wherein the nucleic acid comprises i) a human 5 prime mature guide strand miR-483 having 5, 6, 7, 8, 9, 10, or more continuous nucleotides within 5'-AAGACGGGAG-GAAAGAAGGGAG (SEQ ID NO: 1) and ii) a complementary passenger strand(s) having 5, 6, 7, 8, 9, 10, or more continuous nucleotides with 5'-UCACUCCUCUCCUCCC-GUCUU(SEQ ID NO: 2). In certain embodiments, the nucleic acid stem loop sequence is human miR-483 having 5'-GAGGGGGAAGACGGGAGGAAAGAAGGGAGUG-GUUC CAUCACGCCUCCUCACUCCUCUC CUCCC-GUCUUCUCCUCUC (SEQ ID NO: 3) or operable variants thereof.

In certain embodiments, this disclosure relates to an expression vector that encodes two or three or more nucleic acid sequences in operable combination with a heterologous promoter wherein one nucleic acid has a human 5 prime mature guide strand miR-483 sequence having 5, 6, 7, 8, 9, 10, or more continuous nucleotides within 5'-AAGACGG-GAGGAAAGAAGGGAG (SEQ ID NO: 1) and a second nucleic acid and/or third nucleic acid is a complementary passenger strand having 5, 6, 7, 8, 9, 10, or more continuous nucleotides with 5'-UCACUCCUCUCCUCCCGUCUU (SEQ ID NO: 2).

In certain embodiments, the subject is a risk of, exhibiting symptoms of, or diagnosed with type I or type II diabetes, impaired glucose tolerance, elevated serum C-reactive protein concentration, vitamin B6 deficiency, dietary iodine deficiency, hypothyroidism, hyperlipidemia, hypertension, or is older than 50 years old, or smokes cigarettes daily.

In certain embodiments, a pharmaceutical composition is administered in combination with a statin, atorvastatin, cerivastatin, fluvastatin, lovastatin, mevastatin, pitavastatin, pravastatin, rosuvastatin, simvastatin, ezetimibe, amlodipine, niacin, aspirin, omega-3 fatty acid, or combinations thereof.

In certain embodiments, the disclosure relates to compositions comprising a double stranded nucleobase polymer or RNA consisting of between 15 and 30 continuous nucleotides of SEQ ID NO: 3. In certain embodiments, the double stranded nucleobase polymer or RNA is 3' end capped with one or more thymidine nucleotides and/or the passenger strand of the nucleobase polymer or RNA comprises 5' end phosphate or polyphosphate.

EXAMPLES miRNA-483 Mimic

A miRNA-483 mimic was design based on three RNA strands. The miRNA (guide) strand is an unmodified RNA strand with a sequence corresponding exactly to the annotation in miRBase. The passenger strand is divided in two RNA strands comprising locked nucleotides (HSA-MIR-483-3P). UCACUCCUCUCCUCCCGUCUU (SEQ ID NO: 2).

MicroRNR-483 Expression is Shear-Sensitive and Side-Specific and Inhibits Shear-Induced EndMT and Endothelial Inflammation In microRNA array studies using HAVECs, miR-483 appeared to be a shear-sensitive miRNA, however, its function was unknown. The shear-sensitivity of miR-483 was validated by qPCR in HAVECs. Subjecting HAVECs to OS conditions for 24 hours decreased miR-483 expression by 63% compared to the s-flow condition LS (FIG. 1A).

Figure 1B:
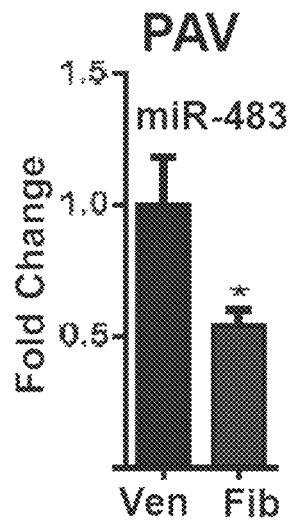
FIG. 1B shows data for endothelial-enriched total RNA from the ventricularis (Ven) and the fibrosa (Fib) side of healthy porcine AVs normalized to U6.

To determine whether miR-483 is expressed in a side-specific manner in AVs, endothelial-enriched RNAs were collected from healthy porcine AVs and miR-483 expression was quantified by qPCR. Endothelial purity levels of these RNA preparations were assessed by measuring markers of macrophages (CD11b), endothelial cells (PECAM1), and VICs (alpha-SMA) by qPCR. Endothelial-enriched RNA preparations showed an abundant level of PECAM1 while the levels of CD11b and alpha-SMA were barely detectable. The level of miR-483 was 45% lower in the fibrosa side (naturally exposed to d-flow conditions) compared to the ventricularis side (naturally exposed to pulsatile, s-flow conditions) (FIG. 1B). These results indicate that miR-483 expression is reduced by OS in HAVECs and in the fibrosa-side where the AV leaflets are exposed to OS.

Figure 1C:
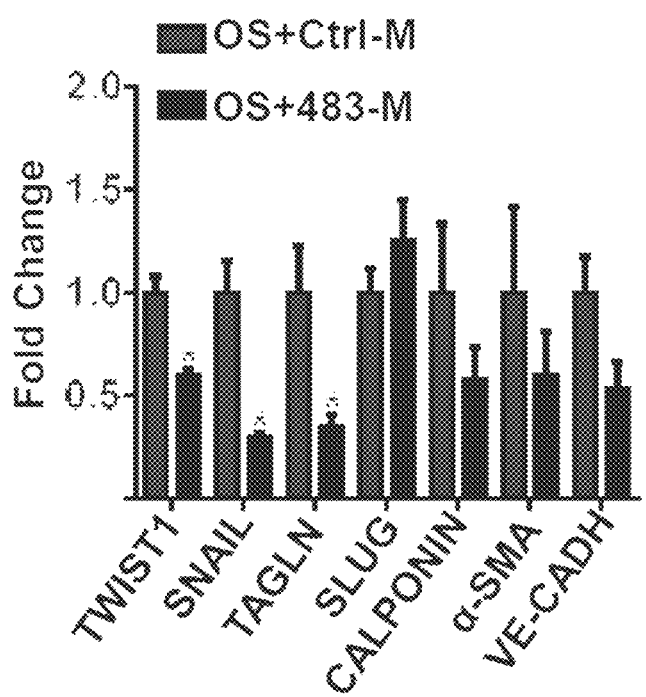
FIG. 1C shows data where HAVECs transfected with miR-483 mimic or anti-miR-483 for 24 hours were exposed to OS for 24 hr. Following shear, total RNAs were prepared for qPCR and analyzed markers of EndMT.
Figure 1D:
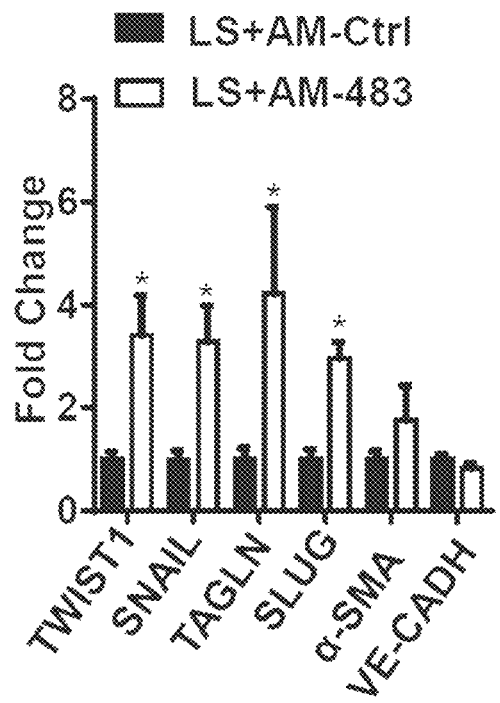
FIG. 1D shows data for EndMT markers when HAVECs are treated with anti-miR-483 (AM-483) and exposed to LS.

Experiments were performed to determine the role of miR-483 in shear-dependent responses of HAVECs by using miR-483 mimic (to overexpress miR-483) or anti-miR-483 (to silence miR-483). HAVECs were treated with miR-483 mimic (20 nM increased miR-483 level by ~200-fold) or anti-miR-483 (50 nM reduced miR-483 level by 80%) for 24 hours, followed by OS or LS for 24 hours, respectively. OS exposure significantly increased expression of EndMT markers (TWIST1, TRANSGELIN (TAGLN), SNAIL and SLUG) (FIG. 1C), which was significantly reduced by treatment with miR-483-mimic in HAVECs. Other markers of EndMT were tested such as calponin, alpha-SMA, and VE-Cadherin. Anti-miR-483 treatment dramatically increased EndMT markers under the LS condition in HAVECs (FIG. 1D), indicating a role of miR-483 in shear-sensitive EndMT.

Figure 1E:
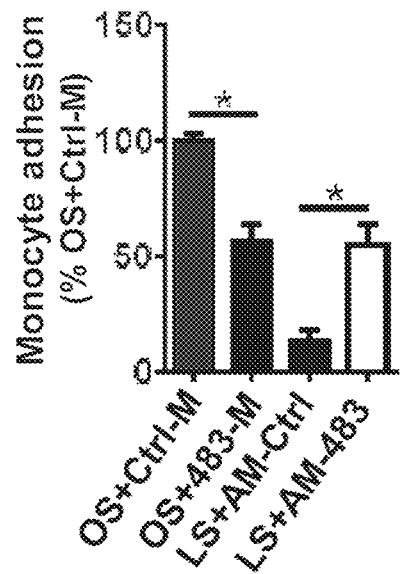
FIG. 1E show data of a THP1 monocyte adhesion assay in HAVECS treated with miR-483 mimic (483-M) or anti-miR-483 (AM-483) and exposure to OS or LS, respectively.
Figure 1F:
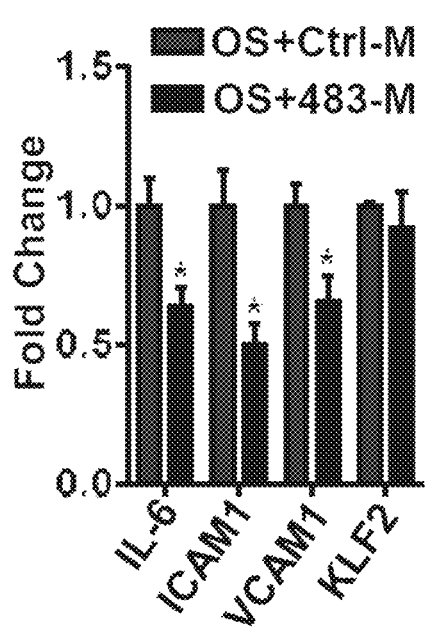
FIG. 1F shows data on inflammation markers when HAVECS are treated with miR-483 mimic (483-M) and exposed to OS.
Figure 1G:
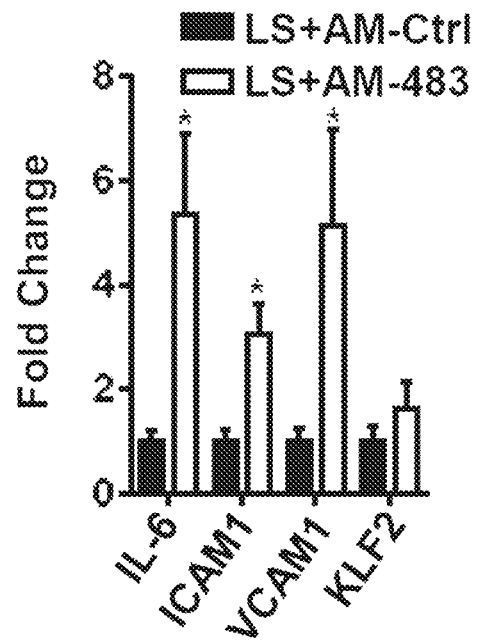
FIG. 1G shows data when HAVECs are treated with anti-miR-483 (AM-483) and exposed to LS.

Experiments were performed to determine whether miR-483 regulates OS-induced endothelial inflammation as determined by monocyte adhesion and expression of pro-inflammatory marker genes (IL6, ICAM1 and VCAM1) (FIGS. 1E, F, G), while using KLF2 (LS-induced anti-inflammatory gene) as a control. Compared to LS, OS induced endothelial inflammation was significantly reduced by miR-483-mimic. In contrast, silencing miR-483 by anti-miR-483 significantly induced endothelial inflammation under the LS condition, indicating a role for miR-483 in shear-dependent endothelial inflammation. Interestingly, neither miR-483-mimic nor anti-miR-483 affected KLF2 expression level (FIGS. 1F and G), suggesting that KLF2 is not a downstream mediator of the miR-483 effect. The anti-inflammatory effect of miR-483 was also confirmed in HAVECs in static (no-flow) conditions. In addition, miR-483-mimic treatment inhibited proliferation of HAVECs, while its silencing increased. On the other hand, miR-483 mimic showed no effect on apoptosis, whereas anti-miR-483 induced apoptosis by 2-fold compared to control. Lastly, miR-483 modulation showed no significant effect on cell migration. Together, these results indicate that reduction in miR-483 level under d-flow condition leads to endothelial inflammation and EndMT, which are implicated in CAVD pathogenesis.

UBE2C is a Shear-Sensitive and Side-Specific Target of miR-483 in HAVECs and in Human AVs To determine the mechanisms by which miR-483 mediates shear-dependent effects on HAVEC function, potential targets of miR-483 were identified. An in silico analysis was performed comparing the predicted targets of miR-483 (950 predicted genes) with OS-induced genes (239 genes) from a HAVEC transcriptome array study. In silico analysis revealed nine genes that were potential gene targets of miR-483 and shear-sensitive genes in our HAVEC transcriptome microarray: ABCB9, ASH2L, DHX33, GADD45B, PSAT1, PSEN2, TMEM88, TOMM20, and UBE2C. To determine whether they are also shear-sensitive, HAVECs were exposed to LS or OS for 24 hours and the expression of these 9 genes was tested by qPCR. This study indicated that OS increased 6 of these 9 genes.

Experiments were performed to determine which of these six shear-sensitive genes were significantly regulated by miR-483 using the miR-483-mimic or anti-miR-483. The results showed that ASH2L, UBE2C and PSAT1 were consistently regulated by the miR-483 modifications in static HAVECs. Experiments were performed to validated if the shear-sensitive expressions of ASH2L, UBE2C and PSAT1 were mediated by miR-483 following treatment of HAVECs with miR-483 mimic under the OS condition or anti-miR-483 under the LS condition. ASH2L and UBE2C were regulated by miR-483 under shear conditions, but PSAT1 was not. These results indicate that ASH2L and UBE2C are shear-sensitive targets of miR-483. Interestingly, knockdown of UBE2C alone dramatically prevented OS-induced endothelial inflammation.

Figures 2A, 2B:
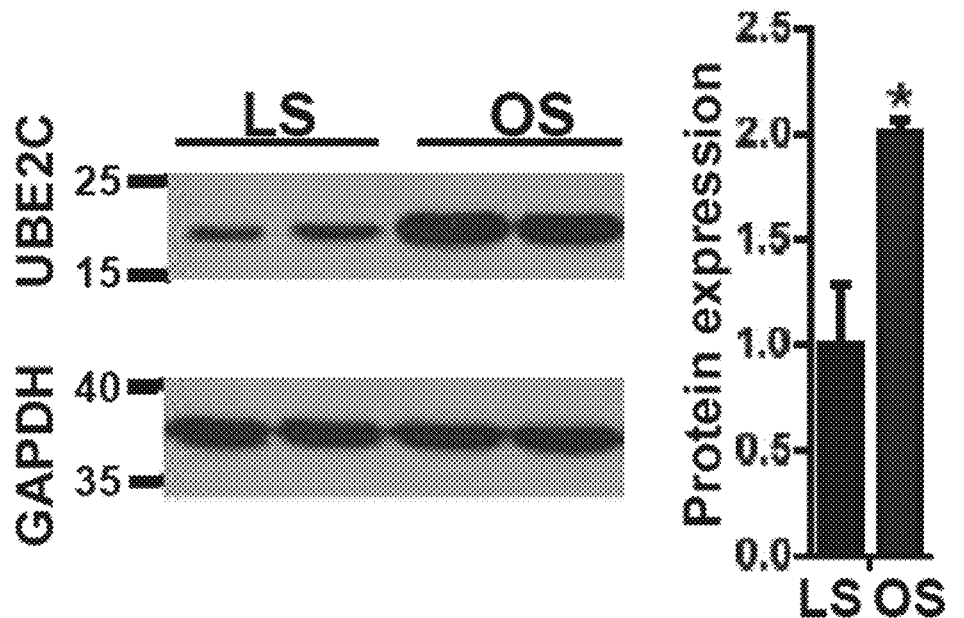
FIG. 2A show data indicating that UBE2C expression was increased in HAVECs exposed to OS compared to LS for 24 hr as determined by Western blot.
FIG. 2B shows quantification data of FIG. 2A.
Figures 2C, 2D:
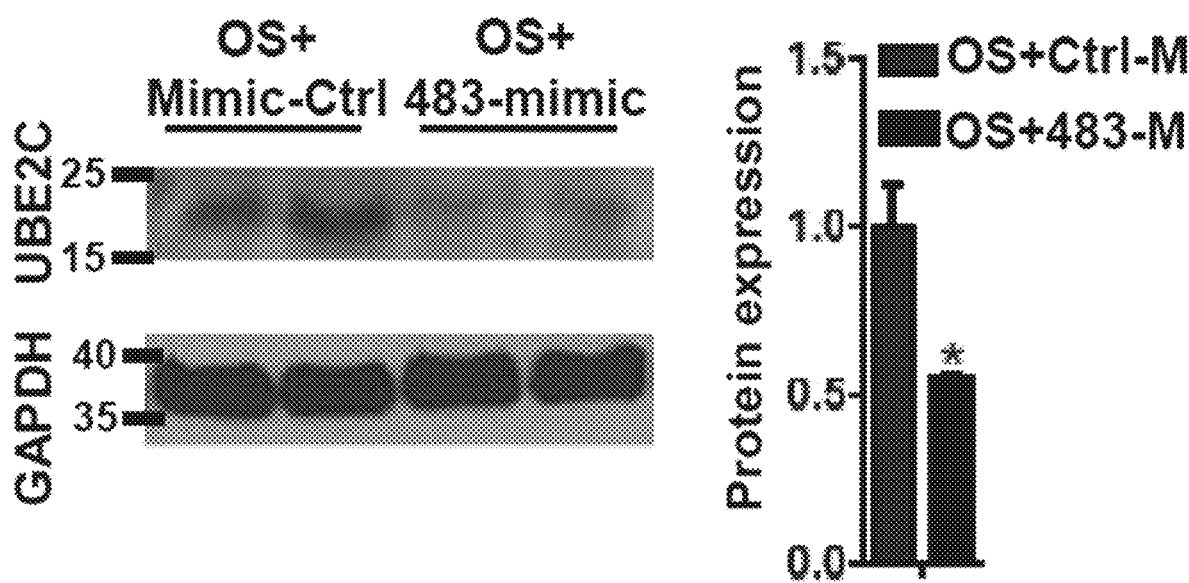
FIG. 2C shows data where HAVECs were treated with miR-483-mimic or mimic control followed by OS and analyzed by UBE2C Western blot.
FIG. 2D shows quantification data of FIG. 2C.
Figure 2E:
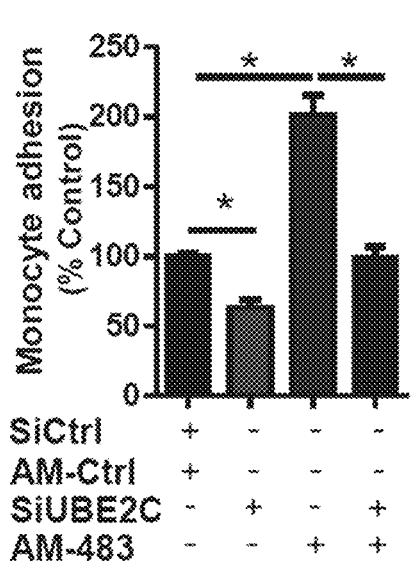
FIG. 2E shows data where HAVECs were co-transfected with siUBE2C or siCtrl and anti-miR-483 (AM-483) or anti-miR-control (AM-Ctrl), followed by THP-1 monocyte adhesion.
Figure 2F:
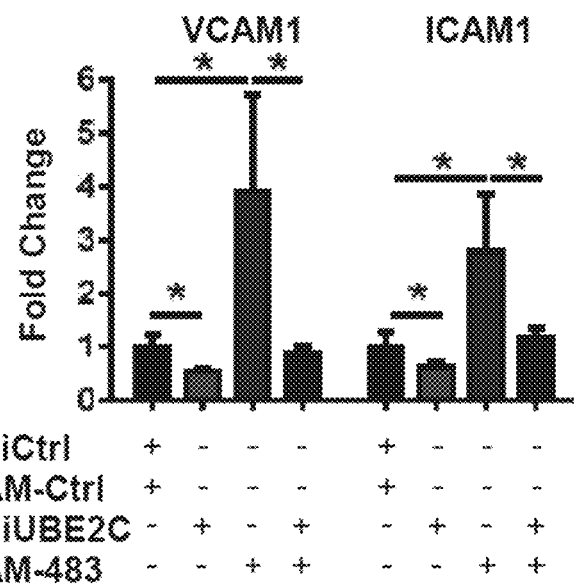
FIG. 2F shows data on qPCR analysis for inflammatory markers for HAVECs co-transfected as in FIG. 2E.
Figure 2G:
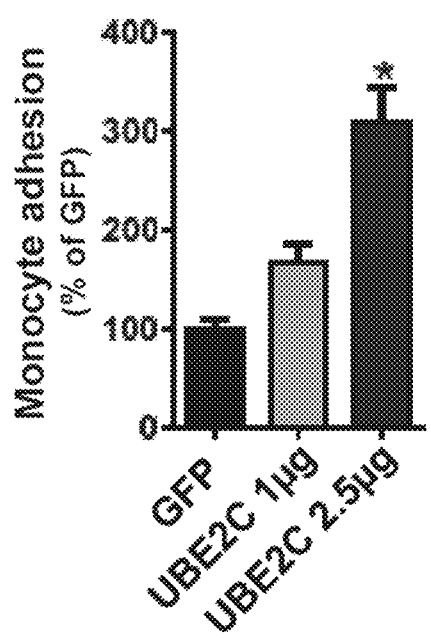
FIG. 2G shows data from a monocyte adhesion assay where HAVECs were transfected with UBE2C overexpression plasmid or a GFP plasmid.
Figure 2H:
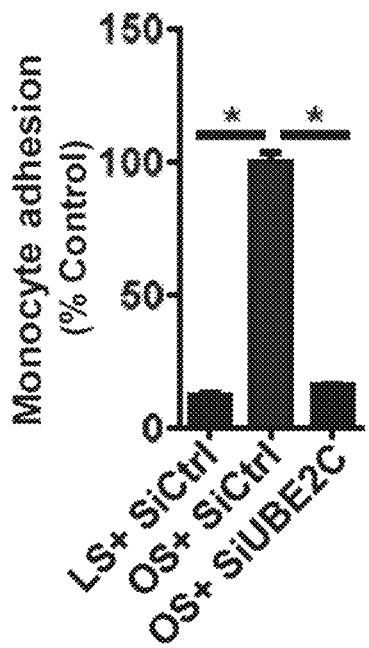
FIG. 2H shows data on monocyte adhesion where HAVECs were treated with siUBE2C or siRNA control (SiCtrl) for 24 hours, followed by OS or LS conditions for another 24 hours.

At the protein level, OS exposure significantly increased UBE2C expression compared to the LS condition in HAVECs (FIGS. 2A and 2B). In addition, the OS-induced increase in UBE2C expression was significantly blocked by miR-483 mimic in HAVECs (FIGS. 2C and 2D), further validating that the reduction of miR-483 by OS leads to de-repression of UBE2C expression. Similar results were observed in static conditions (FIG. 2H).

UBE2C Regulates OS- and miR-483-Dependent Inflammation and EndMT in HAVECs.

Experiments were performed to determine whether UBE2C mediates endothelial inflammation and EndMT by treating HAVECs with UBE2C siRNA (siUBE2C), anti-miR-483 or a combination of both. SiRNA-mediated knockdown of UBE2C inhibited endothelial inflammation in static basal condition as well as in response to anti-miR-483 (to increase UBE2C expression) (FIGS. 2E and 2F). This result suggests that UBE2C mediates the endothelial inflammation induced by the loss of miR-483. Overexpression of UBE2C using the plasmids dose-dependently increased monocyte adhesion in HAVECs (FIG. 2G), further supporting a hypothesis that UBE2C induces pro-inflammatory responses in HAVECs.

Figure 2I:
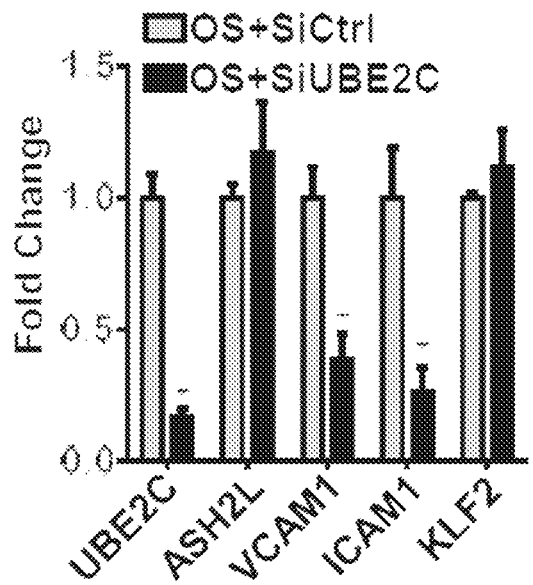
FIG. 2I shows data on qPCR analyses for markers of inflammation for HAVECS treated with siUBE2C and exposed to OS.
Figure 2J:
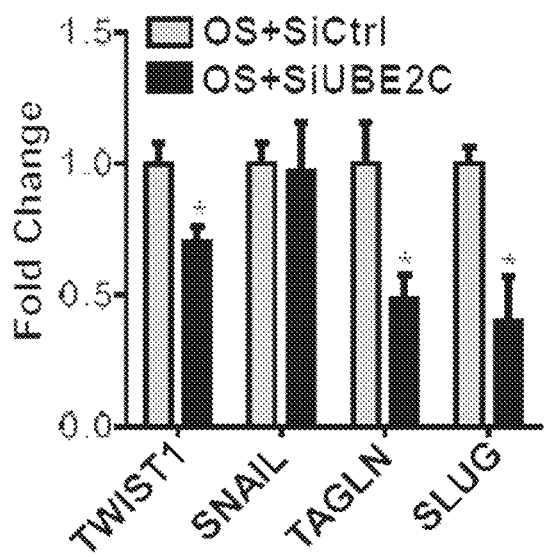
FIG. 2J shows data on EndMT markers for HAVECS treated with siUBE2C and exposed to OS.

Experiments were performed to determine whether OS-induced pro-inflammatory and pro-EndMT responses could be reverted by knockdown of UBE2C using siUBE2C. UBE2C knockdown prevented OS-induced monocyte adhesion and induction of the pro-inflammatory markers (VCAM1 and ICAM1) without affecting KLF2 or ASH2L expression in HAVECs (FIGS. 2H and 2I). Moreover, siUBE2C treatment significantly reduced several markers of EndMT (TWIST1, TAGLN and SLUG) (FIG. 2J). siUBE2C decreases cell proliferation, but not cell migration in HAVECs. Together, these results indicate that UBE2C is a miR-483 target gene, which plays a role in OS-induced pro-inflammatory and pro-EndMT responses in HAVECs.

UBE2C Mediates Flow-Sensitive Expression of pVHL and HIF1alpha.

Figure 3A:
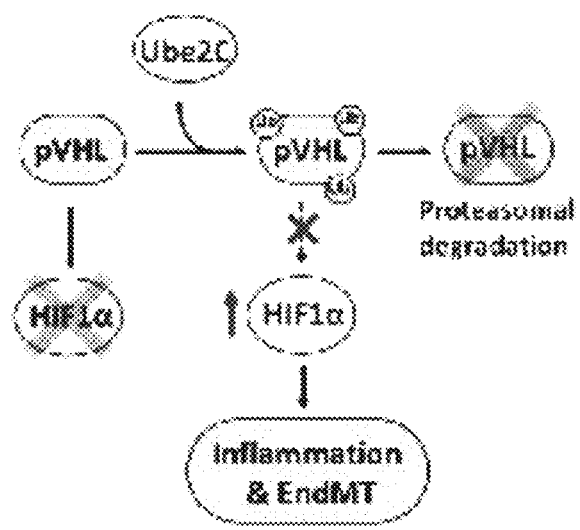
FIG. 3A shows an illustration indicating UBE2C mediates shear-dependent expression of pVHL and HIF1alpha in HAVECs, and UBE2C, pVHL and HIF1alpha are expressed in a side-dependent manner in human AV leaflet. Overexpression of UBE2C ubiquitinates pVHL, leading to increased HIF1alpha level, endothelial inflammation, and EndMT.

Experiments were performed to determine whether an increase in UBE2C (due to the loss of miR-483 under the OS condition) leads to ubiquitination and degradation of pVHL, which in turn increases HIF1alpha levels, leading to increased expression of its target genes, endothelial inflammation and EndMT (FIG. 3A). First, the expressions of pVHL and HIF1alpha were highly shear-sensitive, but inversely regulated in HAVECs. Under LS exposure for 72 hours, expression of pVHL was high, while HIF1alpha expression was undetectable. In contrast, under OS, pVHL was low while HIF1alpha was high at the protein and mRNA levels (FIGS. 3B, 3C, 3D). UBE2C silencing significantly increased pVHL expression while preventing HIF1alpha induction under the OS condition (FIGS. 3E, 3F, 3G 3H), demonstrating that UBE2C regulates shear-dependent expression of pVHL and HIF1alpha.

Figure 3I:
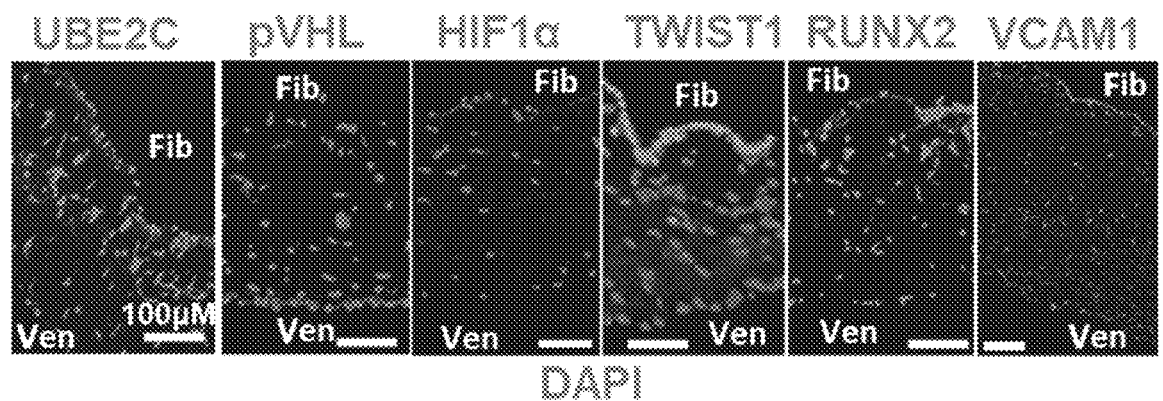
FIG. 3I shows images where human AVs with sclerosis were stained with antibodies to UBE2C, pVHL, HIF1alpha, Twist1, Runx2 and VCAM1 with DAPI nuclear staining.
Figure 3J:
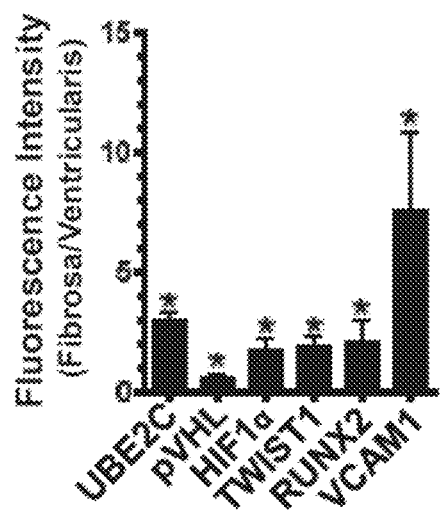
FIG. 3J shows quantification data of the fluorescent intensities of each staining in endothelial layer. Fib: fibrosa, Ven: ventricularis.

Experiments were performed to determine whether the shear-dependent changes in expression of UBE2C, pVHL, and HIF1alpha observed in HAVECs in vitro also occur in diseased human AV leaflets. Molecules such as UBE2C, HIF1alpha, and markers of inflammation, EndMT and calcification are overexpressed in the fibrosa side exposed to disturbed flow (OS). To this end, immunohistochemical staining was performed on human AVs. UBE2C and HIF1alpha expression was significantly higher in the fibrosa-side of the human AV leaflets, whereas pVHL expression was higher in the ventricularis-side (FIGS. 3I and 3J). Furthermore, markers of inflammation (VCAM1), EndMT (TWIST1), and calcification (RUNX2) (FIGS. 3I and 3J) were highly expressed in the fibrosa side demonstrating side-dependent expression of pro-CAVD markers. As a control, endothelial marker CD31 was used showing intact endothelial layers in these AVs. Similar results were obtained in porcine AVs. These staining results corroborate the side-dependent expression of UBE2C, pVHL, and HIF1alpha, with markers of inflammation, EndMT, and calcification in the fibrosa side of human AV leaflets.

UBE2C Binds and Ubiquitinates pVHL, Leading to its Degradation.

Figure 4A:
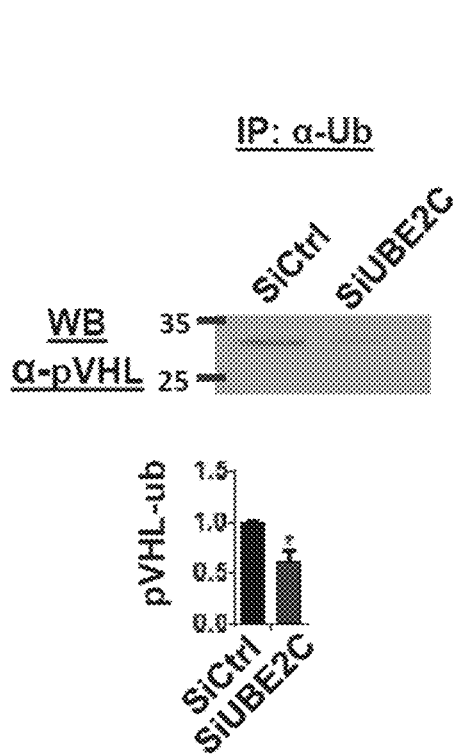
FIG. 4A shows data for HAVECs transfected with siUBE2C or siCtrl and immunoprecipitated with an antibody for ubiquitin (Ub) and Western blotted with the pVHL.
Figure 4B:
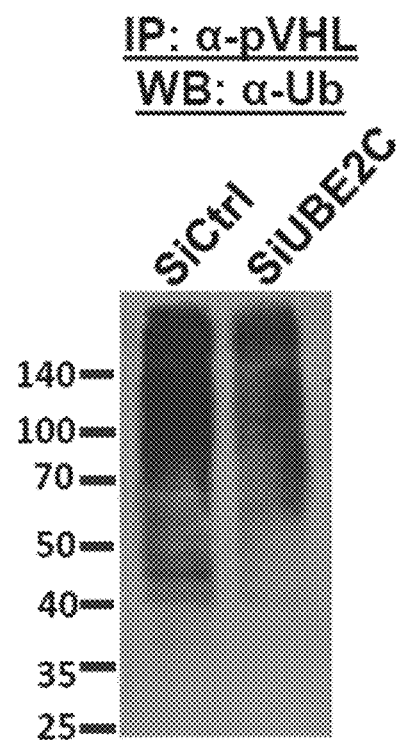
FIG. 4B shows data for HAVECs transfected with siUBE2C or siCtrl and immunoprecipitated with an antibody for pVHL and Western blotted with the ubiquitin (Ub).

Experiments were performed to determine how UBE2C (E2 ubiquitin ligase) regulates pVHL expression. UBE2C is a member of APC/C, which binds and ubiquitinates pVHL for proteasomal degradation. It was unknown whether UBE2C can mediate pVHL ubiquitination. Therefore, whether UBE2C mediates pVHL expression in an ubiquitination-dependent manner was tested. To this end, HAVECs were transfected with siUBE2C, and ubiquitinated proteins were immunoprecipitated and western blotted using a pVHL antibody. Knockdown of UBE2C decreased ubiquitinated pVHL levels in the immunoprecipitated (FIG. 4A). This result was independently validated by immunoprecipitating pVHL first, followed by ubiquitin western blotting, demonstrating that ubiquitination of pVHL was reduced when UBE2C was knocked down in HAVECs (FIG. 4B). Levels of pVHL in these cell lysates were increased.

Figure 4C:
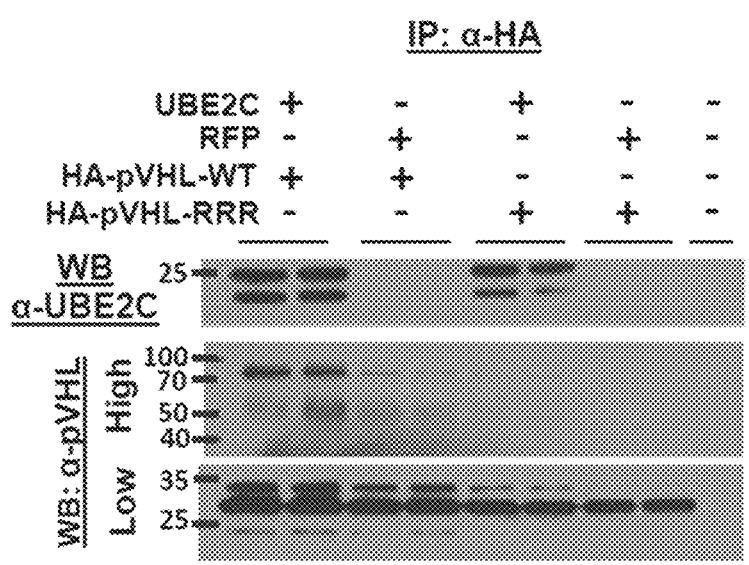
FIG. 4C shows data where HEK cells were co-transfected with myc-UBE2C or RFP plasmid (1 µg) and HA-pVHL-WT or HA-pVHL-RRR mutant plasmids (0.5 µg) for 48 hours were immunoprecipitated using the antibody to HA-tag and Western blotted with the antibody to UBE2C or pVHL (exposed using High intensity ECL and Low intensity ECL). Untreated (Unt) HEK cells were used as a control.
Figure 4D:
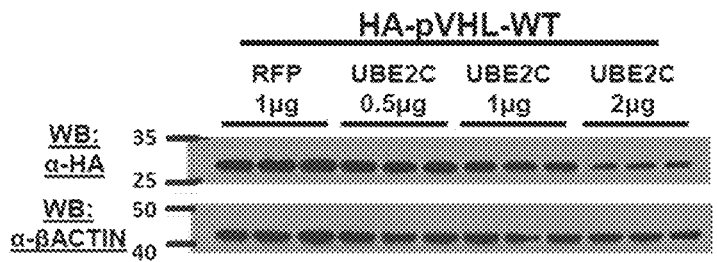
FIG. 4D shows data where HEK cells were co-transfected with HA-pVHL-WT mutant plasmids and increasing dose of UBE2C (0.5-2 µg) or RFP plasmids for 48 hours were lysed and Western blotted with antibodies to pVHL and b-actin as an internal control.
Figure 4E:
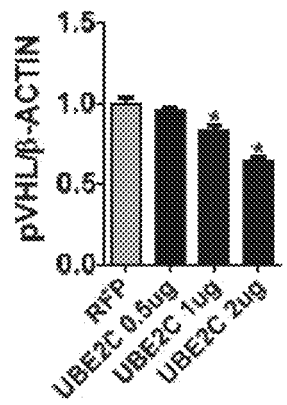
FIG. 4E shows quantification data of FIG. 4D.
Figure 4F:
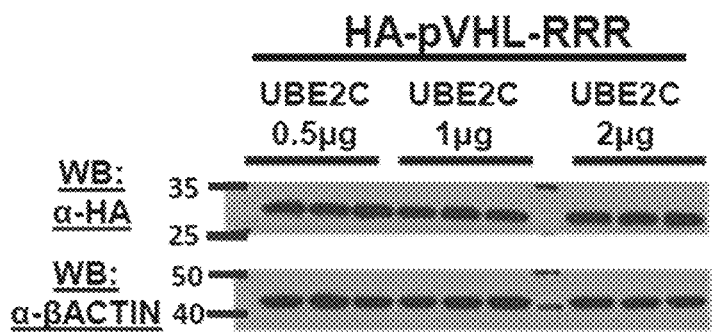
FIG. 4F shows data for where HEK cells were co-transfected with HA-pVHL-RRR mutant plasmids and increasing dose of UBE2C (0.5-2 µg) or RFP plasmids for 48 hours were lysed and Western blotted with antibodies to pVHL and b-actin as an internal control
Figure 4G:
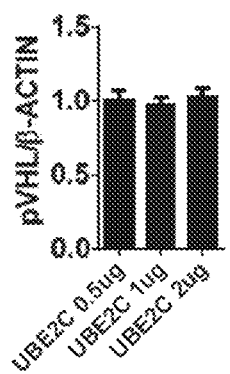
FIG. 4G shows quantification data of FIG. 4F.

Since UBE2C has never been shown to bind and ubiquitinate pVHL, experiments were performed to determine whether they associate with each other by co-transfecting HEK cells with plasmids overexpressing UBE2C or RFP as a control and HA-pVHL-WT or HA-pVHL-RRR mutant. The HA-pVHL-RRR mutant has its three Lys ubiquitination sites (K159, K171 and K196) modified to Arg so that they cannot be ubiquitinated. HA-tag antibody was used to immunoprecipitate HA-pVHL-WT and HA-pVHL-RRR (FIG. 4C). UBE2C co-immunoprecipitated with either HA-pVHL-WT or HA-pVHL-RRR (FIG. 4C). Interestingly, the pVHL Western blot of HA-pVHL immunoprecipitates showed bands at ~28, 34, 55, 80 kDa potentially representing poly-ubiquitinated pVHLs in a manner dependent on UBE2C and pVHL-ubiquitination sites (FIG. 4C). Furthermore, the Western blot using the ubiquitin antibody for the HA-pVHL immunoprecipitates showed ubiquitinated proteins at ~35, 40, 85, 100 kDa in a manner dependent on UBE2C and pVHL-ubiquitination site.

Experiments were performed to determine whether UBE2C regulates pVHL levels in an ubiquitination-dependent manner by co-transfecting HEK cells with plasmids overexpressing UBE2C or RFP control and HA-pVHL WT or mutants. Four different HA-pVHL double or triple mutants on the three Lys ubiquitination sites were used (RRR, KRR, RKR, and RRK) in comparison to WT. Expression of pVHL-WT and the three pVHL double mutants, but not the RRR triple mutant was decreased as UBE2C expression increased in a dose-dependent manner (FIG. 4D-4G). This result indicates that pVHL degradation is UBE2C-dependent on one of the three Lys ubiquitination sites. These results also demonstrate that UBE2C binds to pVHL and mediates its degradation by the ubiquitination-dependent manner.

pVHL and HIF1alpha Mediate UBE2C-Dependent Inflammation and EndMT in HAVECs.

Figure 5A:
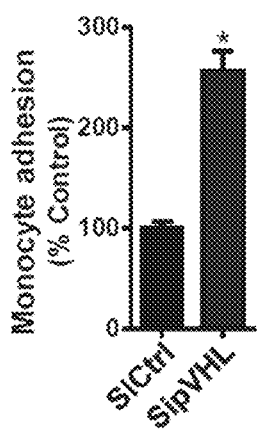
FIG. 5A shows data on monocyte adhesion where HAVECs were transfected with sipVHL.
Figure 5B:
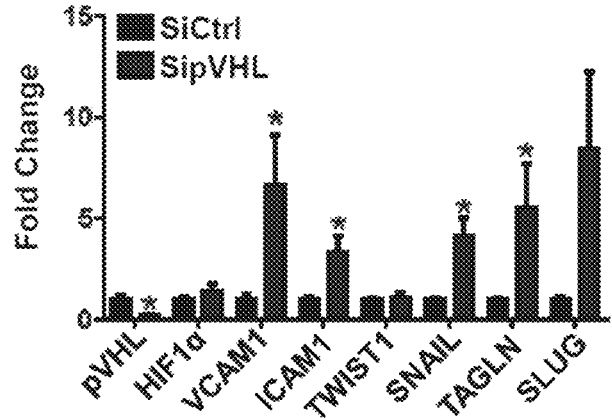
FIG. 5B shows data on qPCR analyses for markers of inflammation and EndMT on HAVECs transfected with siPVHL.
Figure 5C:
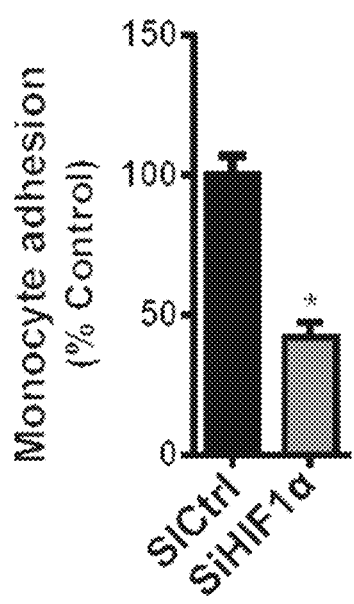
FIG. 5C shows monocyte adhesion on HAVECs transfected with siHIF1Alpha.
Figure 5D:
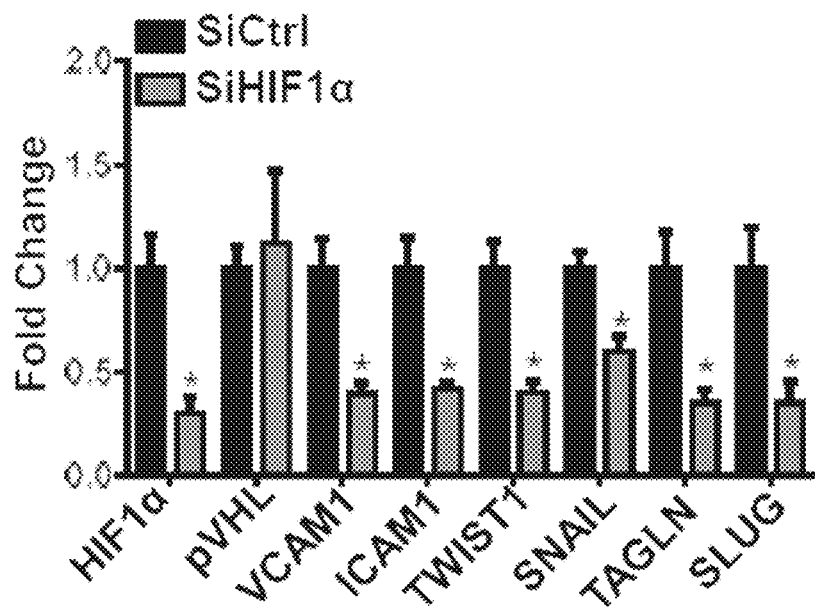
FIG. 5D shows data on qPCR analyses for markers of inflammation and EndMT on HAVECs transfected with siHIF1Alpha.

Experiments were performed to determine whether pVHL and HIF1alpha regulate endothelial inflammation and EndMT by using sipVHL or siHIF1alpha in HAVECs. Knockdown of pVHL increased monocyte adhesion (FIG. 5A) as well as markers of inflammation and EndMT (FIG. 5B). Knockdown of pVHL did not affect HIF1alpha mRNA levels. Knockdown of HIF1alpha inhibited monocyte adhesion (FIG. 5C) and markers of inflammation and EndMT, while not affecting pVHL levels (FIG. 5D).

Figure 5E:
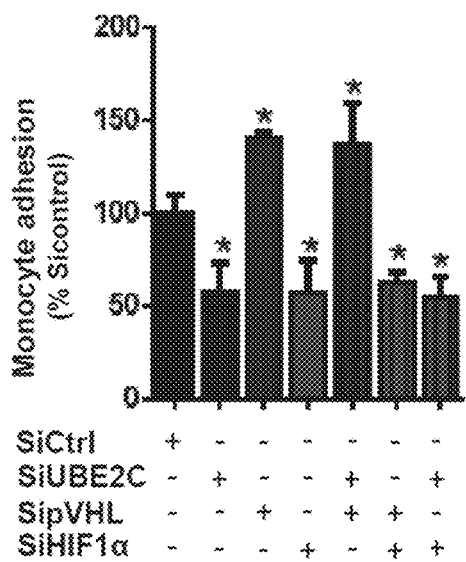
FIG. 5E shows monocyte adhesion when HAVECS are co-transfected with siUBE2C, sipVHL or siHIF1ALPHA for 48 hours.
Figure 5F:
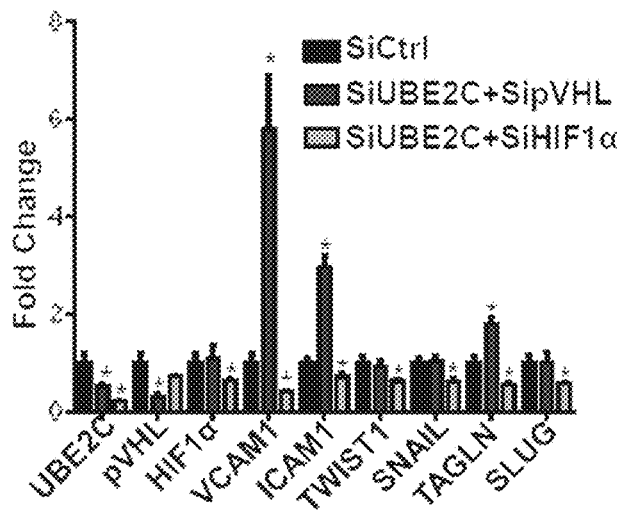
FIG. 5F shows data on qPCR analyses for markers of inflammation and EndMT on HAVECS are co-transfected with siUBE2C, sipVHL or siHIF1ALPHA for 48 hours.

Experiments were performed to determine whether UBE2C-induced endothelial inflammation and EndMT is mediated by either pVHL or HIF1alpha, using siUBE2C, sipVHL or siHIF1alpha in combination. Knockdown of both, UBE2C and pVHL, induced endothelial inflammation and EndMT (FIGS. 5E and 5F). In contrast, silencing of both, UBE2C and HIF1alpha, inhibited inflammation and EndMT (5E and 5F). These results suggest that endothelial inflammation and EndMT, induced by UBE2C, is mediated by pVHL and HIF1alpha in HAVECs.

Figure 6A:
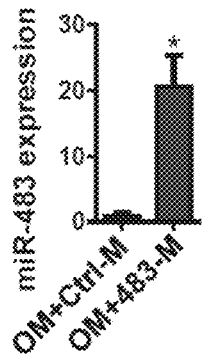
FIG. 6A shows data where freshly harvested porcine AV leaflets were transfected with miR-483 mimic or Ctrl mimic every 3 days for two weeks in osteogenic media (OM). Expression of miR-483 was assessed by qPCR.
Figure 6B:
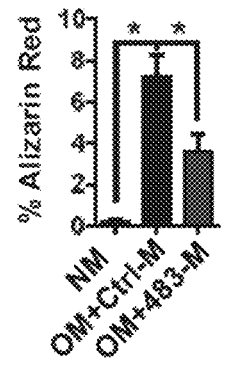
FIG. 6B shows quantification data for immunohistochemical assay using Alizarin Red on PAVs treated with miR-483 mimic in osteogenic media for 14 days.
Figure 6C:
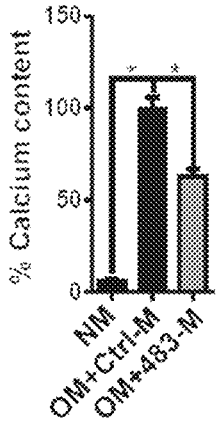
FIG. 6C shows quantification data in the Arsenazo calcium assay on PAVs treated with miR-483 mimic in osteogenic media for 14 days.
Figure 6D:
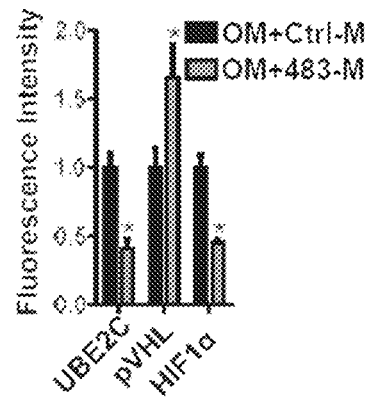
FIG. 6D shows quantification of the fluorescence intensity in porcine AVs treated with miR-483 in osteogenic media immunostained using antibodies for UBE2C, pVHL and HIF1ALPHA.

MiR-483 Mimic and HIF1alpha Chemical Inhibitor PX478 Inhibit Calcification in Porcine Aortic Valves Experiments were performed to determine whether the shear-dependent miR-483, UBE2C, pVHL and HIF1alpha pathway plays a significant role in CAVD. To this end, miR-483 mimic and the HIF1alpha inhibitor PX478 were selected as treatment options. Freshly obtained healthy porcine AV leaflets were cultured in osteogenic media for 14 days to induce calcification (FIG. 6A). Treatment with the miR-483 mimic (20 nM every three days) significantly inhibited AV calcification as measured by Alizarin Red staining (FIG. 6B) and Arsenazo assay (FIG. 6C). The anti-calcific effect of miR-483 was mediated by decreasing UBE2C and HIF1alpha while upregulating pVHL (FIG. 6D).

Figure 6E:
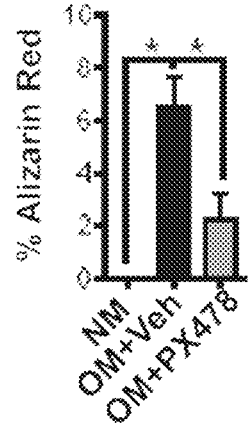
FIG. 6E shows data in the Alizarin red staining where freshly harvested porcine AV leaflets were transfected with PX478 (20 µM) or HBSS vehicle every 3 days for two weeks in osteogenic media (OM).
Figure 6F:
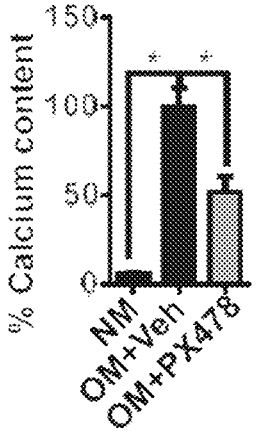
FIG. 6F shows data in the total levels of calcium measured by Arsenazo assay where freshly harvested porcine AV leaflets were transfected with PX478 (20 µM) or HB SS vehicle every 3 days for two weeks in osteogenic media (OM).
Figure 6G:
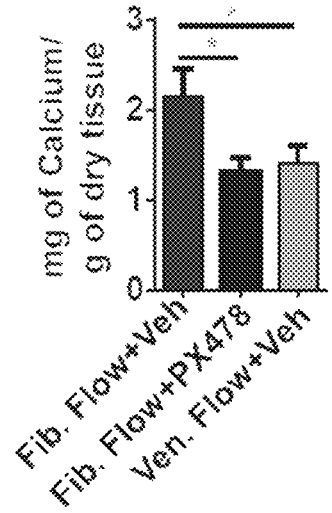
FIG. 6G shows data where porcine AVs were sheared in realistic fibrosa (Fib) or ventricularis (Ven.) shear stress profiles in osteogenic media for 7 days and treated with vehicle or PX478 (20 µM). Total calcium was quantified via Arsenazo assay and normalized to dry tissue weight.

Treatment with PX478 (20 µM every three days) showed a dramatic inhibition of AV calcification (FIG. 6E-6G) and significantly decreased HIF1alpha expression. Additionally, porcine AVs were sheared in realistic fibrosa (Fib.) or ventricularis (Ven.) flow conditions in osteogenic media and treated with PX478 20 µM or vehicle for 7 days. Total calcium levels were quantified via Arsenazo assay. Treatment with PX478 significantly decreased calcium levels in PAVs compared to vehicle control (FIG. 6G). These results demonstrate the therapeutic potential of targeting miR-483 and the HIF1alpha pathway in CAVD and that the effect of HIF1A inhibitor in blocking AV calcification in static conditions is also observed under the disturbed fibrosa-flow condition.

The invention claimed is:

1. A method of treating or preventing atherosclerosis, peripheral vascular disease, or calcific aortic valve disease comprising administering an effective amount of a pharmaceutical composition comprising miR-483 mimic to a subject in need thereof, wherein the miR-483 mimic is a double stranded nucleobase polymer comprising,
   i) a human 5 prime mature guide strand miR-483 having 10 or more continuous nucleobases within 5'-AAGACGGGAGGAAAGAAGGGAG (SEQ ID NO: 1) and
   ii) a complementary passenger strand,
   wherein the complementary passenger strand is a single oligonucleotide comprising 10 or more continuous nucleobases within 5'-UCACUCCUCUCCUCCCGUCUU (SEQ ID NO: 2), or
   wherein the complementary passenger strand is two oligonucleotides that line up to form 10 or more continuous nucleobases within 5'-UCACUCCUCUCCUCCCGUCUU (SEQ ID NO: 2,
   wherein U is individually and independently at each occurrence optionally substituted with T.

2. The method of claim 1, wherein the subject is at risk of, exhibiting symptoms of, or diagnosed with a calcific aortic valve disease (CAVD), atherosclerosis, myocardial infarction, stroke, congestive heart failure, or arrhythmia.

3. The method of claim 1, wherein the miR-483 mimic is administered in combination with a statin.

4. The method of claim 3, wherein the statin is selected from atorvastatin, pravastatin, cerivastatin, lovastatin, mevastatin, pitavastatin, rosuvastatin, simvastatin, and fluvastatin.

5. The method of claim 1, wherein the miR-483 mimic is a double stranded nucleobase polymer comprising:
   a human 5 prime mature guide strand miR-483 consisting of 5'-AAGACGGGAGGAAAGAAGGGAG (SEQ ID NO: 1) and
   a complementary passenger strand consisting of two oligonucleotides that line up to form 5'-UCACUC CUCUC CUC CCGUCUU (SEQ ID NO: 2).

6. The method of claim 1, wherein the double stranded nucleobase polymer comprises a locked nucleobase.

7. The method of claim 1, wherein the locked nucleobase is in the two oligonucleotides of the complementary passenger strand.

8. The pharmaceutical composition of claim 1, wherein the nucleobase polymer comprises monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, 1-(hydroxymethyl)-2,5-dioxabicyclo[2.2.1]heptan-7-yl phosphate, O-(1-(hydroxymethyl)-2,5-dioxabicyclo[2.2.1]heptan-7-yl) phosphorothioate, 5-(hydroxymethyl)-2,6-dioxa-3-azabicyclo[3.2.1]octan-8-ol, 5-(hydroxymethyl)-2,6-dioxa-3-azabicyclo[3.2.1]octan-8-yl phosphate, O-(5-(hydroxymethyl)-2,6-dioxa-3-azabicyclo[3.2.1]octan-8-yl) phosphorothioate, P-(2-(hydroxymethyl)morpholino)-N,N-dimethylphosphoramidate, morpholin-2-ylmethanol, (2-(hydroxymethyl)morpholino) (piperazin-1-yl)phosphinate, or peptide nucleic acids or combinations thereof.

* * * * *